(12) United States Patent
Seyedsayamdost et al.

(10) Patent No.: US 8,673,591 B2
(45) Date of Patent: Mar. 18, 2014

(54) GENETIC INCORPORATION OF 3-AMINOTYROSINE INTO REDUCTASES

(75) Inventors: Mohammad R. Seyedsayamdost, Newton, MA (US); Jianming Xie, Mountain View, CA (US); Clement Tsz Chan, Cambridge, MA (US); Lital Alfonta, San Diego, CA (US); Peter G. Schultz, La Jolla, CA (US); Joanne Stubbe, Arlington, MA (US)

(73) Assignees: The Scripps Research Institute, La Jolla, CA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 12/734,226

(22) PCT Filed: Oct. 23, 2008

(86) PCT No.: PCT/US2008/081024
§ 371 (c)(1),
(2), (4) Date: Jul. 18, 2011

(87) PCT Pub. No.: WO2009/055616
PCT Pub. Date: Apr. 30, 2009

(65) Prior Publication Data
US 2011/0262949 A1    Oct. 27, 2011

Related U.S. Application Data

(60) Provisional application No. 61/000,491, filed on Oct. 25, 2007, provisional application No. 61/001,265, filed on Oct. 30, 2007.

(51) Int. Cl.
C12N 15/67    (2006.01)
C12P 21/02    (2006.01)
C07K 14/00    (2006.01)
C07K 14/505   (2006.01)

(52) U.S. Cl.
USPC .... 435/69.1; 435/199; 435/252.3; 435/320.1; 435/325

(58) Field of Classification Search
None
See application file for complete search history.

(56) References Cited

U.S. PATENT DOCUMENTS

| | | | |
|---|---|---|---|
| 6,927,042 B2 | 8/2005 | Schultz et al. | |
| 7,045,337 B2 | 5/2006 | Schultz et al. | |
| 7,083,970 B2 | 8/2006 | Schultz et al. | |
| 7,129,333 B2 | 10/2006 | Schultz et al. | |
| 7,183,082 B2 | 2/2007 | Schultz et al. | |
| 7,199,222 B2 | 4/2007 | Shultz et al. | |
| 7,217,809 B2 | 5/2007 | Schultz et al. | |
| 7,238,510 B2 | 7/2007 | Schultz et al. | |
| 7,262,040 B2 | 8/2007 | Schultz et al. | |
| 2004/0198637 A1 | 10/2004 | Schultz et al. | |
| 2004/0265952 A1 | 12/2004 | Deiters et al. | |
| 2005/0009049 A1 | 1/2005 | Chin et al. | |
| 2005/0136513 A1 | 6/2005 | Zhang et al. | |
| 2005/0208536 A1 | 9/2005 | Schultz et al. | |
| 2005/0227318 A1 | 10/2005 | Alfonta et al. | |
| 2005/0250183 A1 | 11/2005 | Schultz et al. | |
| 2005/0272121 A1 | 12/2005 | Xie et al. | |
| 2006/0063244 A1 | 3/2006 | Schultz et al. | |
| 2006/0073507 A1 | 4/2006 | Deiters et al. | |
| 2006/0110784 A1 | 5/2006 | Deiters et al. | |
| 2006/0110796 A1 | 5/2006 | Schultz et al. | |
| 2006/0134746 A1 | 6/2006 | Deiters et al. | |
| 2006/0160175 A1 | 7/2006 | Anderson et al. | |
| 2006/0177900 A1 | 8/2006 | Anderson et al. | |
| 2006/0246509 A1 | 11/2006 | Deiters et al. | |
| 2007/0009990 A1 | 1/2007 | Alfonta et al. | |
| 2007/0020634 A1 | 1/2007 | Anderson et al. | |
| 2007/0042461 A1 | 2/2007 | Anderson et al. | |
| 2007/0111193 A1 | 5/2007 | Zhang et al. | |
| 2007/0117184 A1 | 5/2007 | Schultz et al. | |
| 2007/0154952 A1 | 7/2007 | Chin et al. | |
| 2007/0166791 A1 | 7/2007 | Chin et al. | |
| 2007/0172915 A1 | 7/2007 | Schultz et al. | |
| 2007/0178448 A1 | 8/2007 | Tsao et al. | |
| 2007/0184517 A1 | 8/2007 | Schultz et al. | |
| 2007/0238152 A1 | 10/2007 | Wang et al. | |

FOREIGN PATENT DOCUMENTS

JP    2004-261160 A    9/2004
WO   WO 2006/110182 A2   10/2006

OTHER PUBLICATIONS

Tsai et al Rapid Kinetics of Tyrosyl Radical Formation and Heme Redox State Changes in Prostaglandin H Synthase-1 and -2. Jul. 30, 1999 The Journal of Biological Chemistry, 274, 21695-21700.*
ExPASy Protenomics Server Printout, Enzyme entry: Ribonucleotide-diphosphate reductase. Dated Oct. 7, 2010. p. 1-3.
European Search Report, dated Oct. 13, 2010 for EP Application No. 08840980.0.
Wang et al. (2001) "Expanding the genetic code of *Escherichia coli*." *Science*, 292(5516): 498-500.
Xie et al. (2006) "A Chemical Toolkit for Proteins—An expanded Genetic Code" *Nature Reviews Molecular Cell Biology*, 7(10): 775-792.
Bennati et al. (2005) "EPR Distance Measurements Support a Model for Long-Range Radical Initiation in *E. coli* Ribonucleotide Reductase." *Journal of the American Chemistry Society*, 127(43): 15014-15015.
Bollinger Jr., et al. (1995) "Use of Rapid Kinetics Methods to Study the Assembly of the Diferric-Tyrosyl Radical Cofactor of *E. coli* Ribonucleotide Reductase." *Methods in Enzymology*, 258: 278-303.
Climent and Sjöberg (1992) "Site-directed Mutagenesis and Deletion of the Cerboxyl Terminus of *Escherichia coli* Ribonucleotide Redustase protein R2. Effects on Catalytic activity and Subunit Interation." *Biochemistry*, 31(20): 4801-4807.

(Continued)

*Primary Examiner* — Kagnew H Gebreyesus
(74) *Attorney, Agent, or Firm* — Quine IP Law Group, P.C.; Paul Littlepage

(57) ABSTRACT

This invention provides reductase proteins that comprise $NH_2Y$ unnatural amino acid residues, systems of orthogonal elements for incorporating $NH_2Y$ into reductases and methods of using $NH_2Y$ amino acid residues in reductases as molecular probes for probing reductases function, structure and activity.

10 Claims, 12 Drawing Sheets

(56) References Cited

OTHER PUBLICATIONS

Ekberg et al. (1996) "Two Conserved Tyrosine Residues on Protein R1 Participate in an Intermolecular Electron Transfer in Ribonucleotide Reductase." 271(34): 20655-20659.

Högbom et al. (2003) "Displacement of the tyrosyl radical cofactor in ribonucleotide redustase obtained by single-crystal high-field EPR and 1.4-Å x-ray data." *Proceedings of the National Academy of Sciences, USA*, 100(6): 3209-3214.

Jackson et al. (2006) "Improving Nature's Enzyme Active Site with Genetically Encoded Unnatural Amino Acids." *Journal of the American Chemistry Society*, 128(34): 11124-11127.

Kolberg et al. (2005) "A New Tyrosyl Radical on Phe[208] as Ligand to the Diiron Center in *Escherichia coli* Ribonucleotide Reductase, Mutant R3-Y122H." *The Journal of Biological Chemistry*, 280(12): 11233-11246.

Licht et al. (1996) "Thiyl Radicals in Ribonucleotide Redustases." *Science*, 271(5248): 477-481.

Marcus and Sutin (1985) "Electron transfers in chemistry and biology." Biochimica et Biophysica Acta, 811(3): 265-322.

Moser et al. (1992) "Nature of biological electron transfer." *Nature*, 355: 796-802.

Narváez et al. (2006) "The Involvement of Arg[265] of Mouse Ribonucleotide Reductase R2 Protein in Proton Transfer and Catalysis." *The Journal of Biological Chemistry*, 281(36): 26022-26028.

Seyedsayamodost, et al. (2006) "pH Rate Profiles if $F_nY_{356}$-R2s (n=2, 3, 4) in *Escherichia coli* Ribonucleotide Reductase: Evidence that $Y_{356}$ Is a Redox-Active Amino Acid along the Radical Propagation Pathway." *Journal of the American Chemistry Society* 128(5): 1562-1568.

Seyedsayamodost, et al. (2006) "Site-specific Replacement of $Y_{356}$ with 3,4-Dihydroxphenylalanine in the β2 Subunit of *E. coli* Ribonucleotide Reductase." *Journal of the American Chemistry Society*, 128(8): 2522-2523.

Seyedsayamodost, et al. (2007) "Forward and Reverse Election Transfer with the $Y_{356}$DOPA-β2 Heterodimer of *E. coli* Ribonucleotide Reductase." *Journal of the American Chemistry Society*, 129(8): 2226-2227.

Seyedsayamodost, et al. (2007) "PELDOR Spectrosopy with DOPA-β2 and $NH_2Y$-α2s: Distance Measurements between Residues Involved in the Radical Propagation Pathways of *E. coli* Ribonucleotide Reductase." *Journal of the American Chemistry Society*, 129: 15748-15749.

Seyedsayamodost, et al. (2007) "Site-specific incorporation of fluorotyrosines into the R2 subunit of *E. coli* ribonucleotide reductace by ligation." *Nature Protocols*, 2(5): 1225-1235.

Seyedsayamodost, et al. (2007) "Site-specific insertion of 3-aminotryrosine into subunit alpha2 of *E. coli* ribonucleotide reductase: direct evidence for involvement of Y730 and Y731 in radical propagation." *Journal of the American Chemistry Society*, 129(48): 15060-15071.

Sjöberg and Reichard (1978) "The Tyrosine Free Radical in Ribonucleotide Redustase from *Escherichia coli*." *Journal of Biological Chemistry*, 253(19): 6863-6865.

Stubbe et al. (2003) "Radical Initiation in the Class I Ribonucleotide Redustase: Long-Range Proton-Coupled Electron Transfer?" *Chemical Reviews*, 103(6): 2167-2201.

Ven Der Donk et al. (1995) "EPR Investigations of the Inactivation of *E. coli* Ribonucleotide Redutase with 2'-Azido-2'-deoxyuridine '-Diphosphate: Evidence for the Involvement of the Thiyl Radical of C225-R1." *Journal of the American Chemistry Society*, 117(35): 8908-8916.

Yee et al. (2003) "2,3-Difuorotyrosine at Position 356 of Ribonucleotide Reductase R2: A Probe of Long-Range Proton-Coupled Electron Transfer." *Journal of the American Chemistry Society*, 125(33): 10506-10507.

Yee et al. (2003) "Generation of the R2 Subunit of Ribonucleotide Reductase by Intein Chemistry: Insertion of 3-Nitrotyrosine at Residue 356 as a Probe of the Radical Initiation Process." *Biochemistry*, 42(49): 14541-14552.

\* cited by examiner

Scheme 1:

Nucelotide Sequences

| SEQ ID NO: | Description | SEQUENCE |
|---|---|---|
| 1 | Primer for amplifying *nrdA* gene | AT AAT TGG TAC CCA AAA ACA GGT ACG ACA TAC ATG AAT C |
| 2 | Primer for amplifying *nrdA* gene | GCT GCA GGT CGA CTC TAG AGG ATC CCC CCT TCT TAT C |
| 3 | Primer for introducing TAG codon into position 730 α2 | G GTC AAA ACA CTG TAG TAT CAG AAC ACC CG |
| 4 | Primer for introducing TAG codon into position 730 of α2 | CG GGT GTT CTG ATA CTA CAG TGT TTT GAC C |
| 5 | Primer for introducing TAG codon into position 731 of α2 | G GTC AAA ACA CTG TAT TAG CAG AAC ACC CG |
| 6 | Primer for introducing TAG codon into position 731 of α2 | CG GGT GTT CTG CTA ATA CAG TGT TTT GAC C |

GENETIC INCORPORATION OF 3-AMINOTYROSINE INTO REDUCTASES

CROSS-REFERENCE TO RELATED APPLICATIONS

This application is a 371 application of PCT/US2008/081024, filed Oct. 23, 2008, and which claims priority to and benefit of U.S. Provisional Patent Application Ser. No. 61/000,491, filed on Oct. 25, 2007, and Provisional Patent Application Ser. No. 61/001,265, filed on Oct. 30, 2007, the contents of which are hereby incorporated by reference in their entirety for all purposes.

SPONSORED RESEARCH AND DEVELOPMENT

This invention was made with government support from the National Institutes of Health under Grant No. 5R01 GM62159 and Grant No. GM29595. The government has certain rights in this invention.

FIELD OF THE INVENTION

This invention relates to the field of protein chemistry, e.g., translation biochemistry and mutation analysis. The invention relates to methods and compositions for producing a reductase enzyme comprising a 3-aminotyrisone residue and for determining the function of a selected amino acid residue in a reductase.

BACKGROUND OF THE INVENTION

In all organisms, ribonucleotide reductases (RNRs) catalyze the conversion of nucleotides to 2'-deoxynucleotides, providing the precursors used in DNA biosynthesis and repair.[1-3] The mechanism of nucleotide reduction is conserved in all RNRs and requires formation of a transient active site thiyl radical ($C_{439}$., E. coli RNR numbering used throughout the text).[4,5] However, the mechanism of active site thiyl radical generation, the radical initiation event, is not conserved and provides the basis for distinction between four classes of RNRs.[6-9] A major unresolved mechanistic issue is that of thiyl radical formation in class I RNRs, and presumably in the recently identified class IV RNRs.

The E. coli class I RNR consists of two homodimeric subunits, α2 and β2, which form an active 1:1 complex during turnover.[10-12] α2 is the business end of the complex. It contains the active site where thiyl radical-mediated nucleotide reduction occurs, as well as multiple allosteric effector binding sites which modulate substrate specificity and turnover rate.[13] β2 houses the stable diferric tyrosyl radical ($Y_{122}$.)[14-16] cofactor that is required for formation of the transient $C_{439}$. in the active site of α2.[4-6] The structures of α2[6,17] and β2[18,19] have been solved and a structure containing both subunits has also been reported.[20] A structure of the active α2β2 complex, however, has remained elusive. From the individual structures of α2 and β2, Uhlin and Eklund have generated a docking model of the α2β2 complex based on shape and charge complementarity and conserved residues.[6] This model suggests that the $Y_{122}$. in β2 is located >35 Å away from $C_{439}$ in α2 (FIG. 1).[21-23] Radical propagation over this long distance requires the involvement of transient amino acid intermediates.[24-26] The residues proposed to participate in this pathway are universally conserved in all class I RNRs.

Evidence in support of the long distance between $Y_{122}$. and $C_{439}$ has recently been obtained from pulsed electron-electron double resonance spectroscopic measurements[27] with a mechanism based inhibitor.[28-32] The distance obtained from this study is consistent with the docking model and establishes that a large conformational change, that positions $Y_{122}$. in β2 adjacent to $C_{439}$ in α2, does not occur.[32]

To examine the validity of the proposed pathway, site-directed mutagenesis[33,34] and complementation studies[35] have been carried out. These studies demonstrate that each residue in FIG. 1 plays an important role in RNR function. However, the absence of activity in these mutants precludes mechanistic investigations.[33,34] At present, evidence, e.g., detailed elsewhere herein, for the involvement of only one of the proposed pathway residues, $Y_{356}$, is substantial. In contrast, the roles of α2 residues $Y_{730}$ and $Y_{731}$ in radical propagation are still ill-defined. Mutagenesis studies have demonstrated their importance in RNR function.[34,44,45] However, as with residue $Y_{356}$ in β2, the inactivity of these mutants ($Y_{730}$F—α2 and $Y_{731}$F-α2) precluded mechanistic interrogation of the role of $Y_{730}$ and $Y_{731}$ in radical propagation.

What is needed in the art are methods and compositions for the site-specific replacement of an amino acid residue that is proposed to participate in radical propagation in a reductase enzyme with unnatural amino acid residue that produces a mechanistically informative mutant, e.g., a mutant that can be used to interrogate the replaced amino acid's function in radical propagation in, e.g., a reductase enzyme. The present invention provides new tools and methods for elucidating RNR reaction mechanisms.

SUMMARY OF THE INVENTION

The invention relates to recombinant reductase enzymes that include a 3-aminotyrosine ($NH_2Y$) residue, as well as orthogonal systems of components for producing such reductase enzymes. These tools were used to demonstrate kinetically competent radical transfer in E. coli RNR from $Y_{122}$. in the β2 subunit of the RNR across the subunit interface, and also radical trapping of $NH2Y_{730}$. or $NH2Y_{731}$. This event was shown to be triggered by binding of substrate and effector by the E. coli RNR. Steady state activity assays in conjunction with reactions with the suicide inhibitor N3ADP indicate that $Y_{730}NH2Y$-α2 and $Y_{731}NH2Y$-α2 are competent in nucleotide reduction. This implicates a hydrogen atom transfer mechanism for oxidation of $C_{439}$ by $NH2Y_{730}$.

Accordingly, in a first aspect, the invention provides recombinant reductase enzymes that comprise a 3-aminotyrosine ($NH_2Y$) residue. In one preferred embodiment, a reductase of the invention is or is derived from a ribonucleotide reductase, such as a class I or class IV ribonucleotide reductase. For example, the reductase can be a recombinant reductase derived from an E. coli ribonucleotide reductase, a human ribonucleotide reductase, a mouse ribonucleotide reductase, a yeast ribonucleotide reductase, a herpes simplex virus ribonucleotide reductase, or the like. For example, the reductase can be an E. coli ribonucleotide reductase comprising an $NH_2Y$ mutation at one or more of $Y_{730}$ of an α2 subunit of the E. coli ribonucleotide reductase; $Y_{731}$ of an α2 subunit of the E. coli ribonucleotide reductase; $Y_{122}$ of an β2 subunit of the E. coli ribonucleotide reductase; or $Y_{356}$ of a β2 subunit of the E. coli ribonucleotide reductase.

In a related aspect, the invention provides cells that express a reductase of the invention. A cell of the invention includes a recombinant nucleic acid that is derived from a reductase nucleic acid that encodes one or more polypeptide chain of a reductase enzyme, an orthogonal tRNA (O-tRNA), and an orthogonal aminoacyl tRNA synthetase (O-RS). Optionally, the cell can include 3-aminotyrosine. The orthogonal aminoacyl tRNA synthetase (O-RS) in the cell preferentially aminoacylates the O-tRNA with 3-aminotyrosine in the cell, and the recombinant nucleic acid encoding the reductase includes a selector codon that is recognized by the orthogonal tRNA (O-tRNA). The encoded reductase can optionally comprise a class I or class IV ribonucleotide reductase (RNR) and/or an RNR derived from E. coli.

In addition, the invention provides for high yields of reductases comprising $NH_2Y$ residues. For example, a cellular paste or extract that includes a recombinant reductase enzyme, e.g., a recombinant ribonucleotide reductase, comprising the 3-aminotyrosine ($NH_2Y$) residue can be produced, in which the cellular paste or extract comprises at least about 2 and about 4 mg/g of the reductase enzyme. In one example herein, the cellular paste comprises between about 4 and about 6 mg/g of the reductase enzyme.

In another aspect, the invention includes methods of determining a mechanistic function of a selected amino acid residue in a reductase. Such methods include mutating the selected amino acid residue to 3-aminotyrosine ($NH_2Y$) to produce a recombinant mutant reductase that comprises $NH_2Y$ at a site corresponding to the selected amino acid (e.g., a Y residue), mixing the recombinant reductase with one or more substrates or effectors of the reductase, and detecting formation of $NH_2Y$. For example, where the reductase is RNR, the substrate can optionally include CDP ADP, GDP, or UDP and the effector can include ATP. The reductase can optionally be reduced (or oxidized, depending on the application) prior to said mixing. Reducing the recombinant reductase can optionally include purifying the recombinant reductase from a cell, cell paste, or cell culture that expresses the recombinant reductase, and incubating the resulting purified reductase with a reducing agent.

Detecting formation of $NH_2Y$ can include any of a variety of techniques, including determining an EPR spectra for the $NH_2Y$ residue in the reductase, performing stopped flow spectroscopy after mixing to determine the kinetics of $NH_2Y$. formation, or performing rapid freeze quench (RFQ) EPR after mixing to determine the kinetics of $NH_2Y$. formation.

It will be appreciated that methods and compositions provided by the invention can be used alone or in combination.

Kits are also a feature of the invention. For example, such kits can comprise various components selected from: a container to hold the kit components, instructional materials for producing (e.g., expressing and/or purifying) a reductase enzyme, e.g., any of the reductase enzymes described herein, comprising one or more 3-aminotyrosine, a nucleic acid comprising a polynucleotide sequence encoding an O-tRNA, a nucleic acid comprising a polynucleotide encoding an O-RS, 3-aminotyrosine, and/or a suitable strain of E. coli host cells for expression of the O-tRNA/O-RS and production of a reductase enzyme comprising 3-aminotyrosine. Additionally or alternatively, kits of the invention can comprise instructions and/or reagents for determining a function of a selected amino acid residue, e.g., in free radical propagation, in a reductase.

BRIEF DESCRIPTION OF THE FIGURES

FIG. 18 provides various nucleotide sequences finding use with the invention.

DETAILED DESCRIPTION OF THE INVENTION

Figure 1:
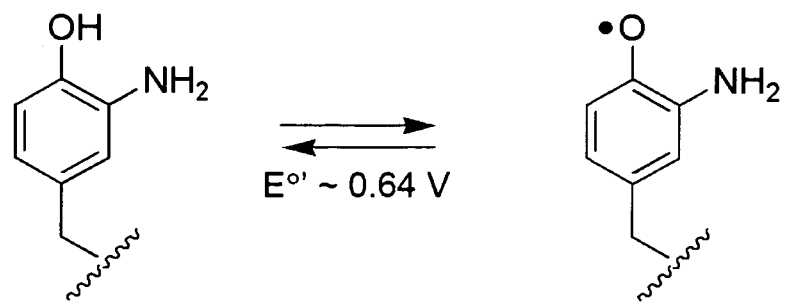
FIG. 1 includes Scheme 1, which depicts one electron oxidation of $NH_2Y$, and a putative radical initiation pathway.
Figure 1:
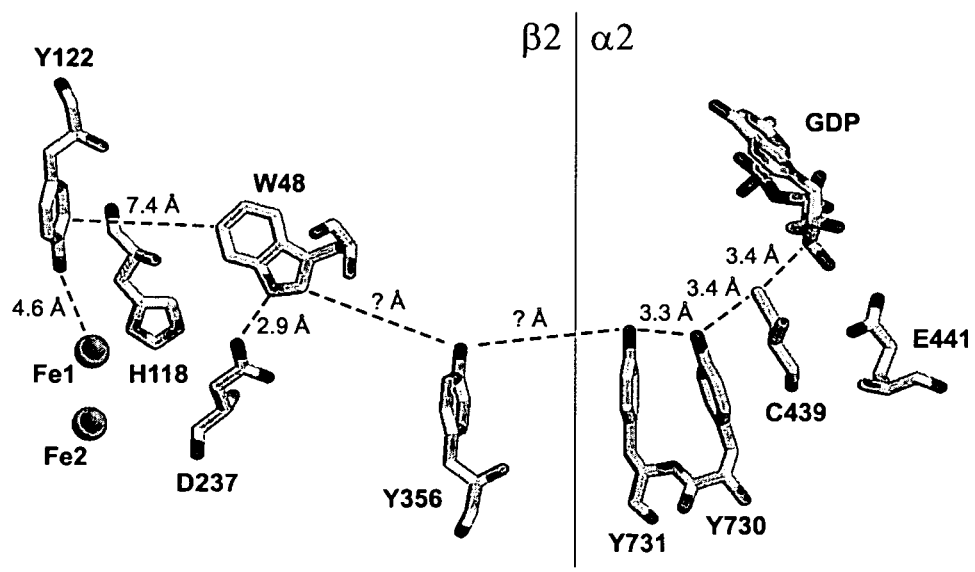

The present invention is directed to reductases, such as ribonucleotide reductases, that comprise 3-aminotyrosine ($NH_2Y$) residues. The $NH_2Y$ residue can be incorporated into a reductase using a system of orthogonal elements that comprises an aminoacyl tRNA synthetase specific for 3-aminotyrosine ($NH_2Y$), an O-tRNA, and, optionally, the unnatural amino acid 3-aminotyrosine. Methods and compositions for producing such recombinant reductases and compositions that comprise high yields of these recombinant reductases are described in further detail hereinbelow.

Once incorporated into a reductase, e.g., any one of the reductases described hereinbelow, the $NH_2Y$ can advantageously serve as a probe for analyzing the mechanistic role of the natural amino acid it replaced in radical propagation in the reductase enzyme (see, for example, FIG. 1 and corresponding description). In general, this can be accomplished by detecting the formation of the unnatural amino acid radical intermediate $NH_2Y$., e.g., via EPR, rapid-freeze-quench EPR, and/or stopped flow spectrometry.

Systems of Orthogonal Elements for $NH_2Y$ Incorporation

Orthogonal components for the incorporation of, e.g., $NH_2Y$, have been described previously; see WO 2006/110182 A2 by Schultz et al. ORTHOGONAL TRANSLATION COMPONENTS FOR THE VIVO INCORPORATION OF UNNATURAL AMINO ACIDS. In general, synthetases with the desired $NH_2Y$ specificity can be produced by randomly or selectively mutating the active site of an existing synthetase and selecting the resulting library of mutant synthetases to screen for desired NH$_2$Y incorporation activity. Typically, libraries are positively screened for NH$_2$Y incorporation and then negatively screened to eliminate members that aminoacylate a tRNA with natural amino acids. Iterative rounds of positive and negative selection can be performed to obtain the synthetase, e.g., a synthetase with a specificity for NH2Y. Additional details regarding screening and selection of O-RS to identify those that aminoacylate a cognate O-tRNA with NH$_2$Y can be found in the examples below.

The reductase enzymes of the invention optionally include additional unnatural amino acids, in addition to the NH$_2$Y unnatural amino acid. In general, using systems of orthogonal components, it is possible to put, e.g., 1, 2, 3, 4, 5, or more different unnatural amino acids into, e.g., 1, 2, 3, 4, 5, or more selected sites in proteins, e.g., by including a desired selector codon in a corresponding nucleic acid. A cell can include, e.g., 1, 2, 3, 4, 5, or more different sets of cognate orthogonal components that each recognize a different given selector codon (stop codons and four or more base codons can be used as selector codons).

Details regarding methods for producing and/or altering the specificity of tRNAs and/or O-RSs, unnatural amino acids, selector codons, and orthogonal translation systems that are suitable for making proteins that include one or more unnatural amino acids are generally described in, for example, International Publication Numbers WO 2002/086075, entitled "METHODS AND COMPOSITION FOR THE PRODUCTION OF ORTHOGONAL tRNA-AMINOACYL-tRNA SYNTHETASE PAIRS;" WO 2002/085923, entitled "IN VIVO INCORPORATION OF UNNATURAL AMINO ACIDS;" and WO 2004/094593, entitled "EXPANDING THE EUKARYOTIC GENETIC CODE;" WO 2005/019415, filed Jul. 7, 2004; WO 2005/007870, filed Jul. 7, 2004 and WO 2005/007624, filed Jul. 7, 2004. Each of these applications is incorporated herein by reference in its entirety. See also, Wang and Schultz "Expanding the Genetic Code," *Angewandte Chemie Int. Ed.*, 44(1): 34-66 (2005); Deiters et al, *Bioorganic & Medicinal Chemistry Letters* 15:1521-1524 (2005); Chin et al., *J. Am. Chem. Soc.* 2002, 124, 9026-9027; and International Publication No. WO2006/034332, filed on Sep. 20, 2005, the contents of each of which are incorporated by reference in their entirety. Additional details are found in U.S. Pat. No. 7,045,337; No. 7,083,970; No. 7,238,510; No. 7,129,333; No. 7,262,040; No. 7,183,082; No. 7,199,222; and No. 7,217,809.

Reductases

A reductase is an enzyme that catalyses a reduction reaction. However, most reductases can, under the proper conditions, behave as reductases or oxidases. Accordingly, the term oxidoreductase is also used to describe this broad family of enzymes, any of which can be modified according to the present invention to include, e.g., one or more NH$_2$Y residue. In general, this is accomplished by incorporating an appropriate selector codon into a nucleic acid that encodes the reductase and expressing the reductase in a cell that includes an appropriate O-RS specific for NH$_2$Y, a cognate O-tRNA that recognizes the selector codon, and NH$_2$Y.

Examples of reductase enzymes that can be modified in this way to include an NH$_2$Y residue include those with Enzyme Commission number (EC number) "EC1." This includes EC 1.1 (oxidoreductases that act on the CH—OH group of donors (e.g., alcohol oxidoreductases); EC 1.2 (oxidoreductases that act on the aldehyde or oxo group of donors); EC 1.3 oxidoreductases that act on the CH—CH group of donors (e.g., CH—CH oxidoreductases); EC 1.4 (oxidoreductases that act on the CH—NH$_2$ group of donors (Amino acid oxidoreductases, Monoamine oxidase); EC 1.5 (oxidoreductases that act on CH—NH group of donors); EC 1.6 (oxidoreductases that act on NADH or NADPH); EC 1.7 (oxidoreductases that act on other nitrogenous compounds as donors) EC 1.8 (oxidoreductases that act on a sulfur group of donors); EC 1.9 (oxidoreductases that act on a heme group of donors), EC 1.10 (oxidoreductases that act on diphenols and related substances as donors) EC 1.11 (oxidoreductases that act on peroxide as an acceptor (e.g., peroxidases)); EC 1.12 (oxidoreductases that act on hydrogen as donors); EC 1.13 (oxidoreductases that act on single donors with incorporation of molecular oxygen (e.g., oxygenases)); EC 1.14 (oxidoreductases that act on paired donors with incorporation of molecular oxygen); EC 1.15 (oxidoreductases that act on superoxide radicals as acceptors); EC 1.16 (oxidoreductases that oxidize metal ions); EC 1.17 (oxidoreductases that act on CH or CH2 groups); EC 1.18 (oxidoreductases that act on iron-sulfur proteins as donors); EC 1.19 (oxidoreductases that act on reduced flavodoxin as a donor); EC 1.20 (oxidoreductases that act on phosphorus or arsenic in donors); EC 1.21 (oxidoreductases that act on X—H and Y—H to form an X—Y bond); EC 1.97 (other oxidoreductases); EC 1.98 (enzymes using H$_2$ as a reductant); and EC 1.99 (enzymes using O$_2$ as an oxidant).

One particularly preferred embodiment of the invention relates to the incorporation of NH$_2$Y into the reductases of EC 1.17 (reductases acting on CH or CH2 groups), including xanthine oxidases and, especially, ribonucleotide reductases (RNRs). Ribonucleotide reductases (RNRs can catalyze the reduction of ribonucleotides, e.g., CDP, ADP, GDP, and UDP, to deoxyribonucleotides in all organisms. Because RNRs maintain the relative ratios of cellular dNTP levels, these enzymes play a central role in nucleic acid metabolism, DNA repair, genome maintenance, and cell proliferation (Sjoberg (1997) "Ribonucleotide reductases—a group of enzymes with different metallosites and a similar reaction mechanism." *Struct Bonding (Berlin)* 88: 139-173; Reichard (1993) "From RNA to DNA, why so many reductases?" *Science* 260: 1773-1777). (dTDP is produced by thymidilate synthase). The mechanism by which RNRs reduce NDPs involves complex and highly regulated radical-dependent redox chemistry (Stubbe (1990) "Ribonucleotide reductases: amazing and confusing." *J Biol Chem* 265: 5329-5332; Jordan, et al. (1998) "Ribonucleotide reductases." *Annu Rev Biochem* 67: 71-98). In general, RNRs, except those of herpesviruses, are allosterically regulated by deoxyribonucleoside triphosphates and ATP, such that DNA precursors are supplied in pools balanced according to the base composition of the different genomes (Hendricks, et al. (1997) "Regulation of T4 phage aerobic ribonucleotide reductase. Simultaneous assay of the four activities." *J Biol Chem* 272: 2861-2865; Hendricks, et al. (1998) "Allosteric regulation of vaccinia virus ribonucleotide reductase, analyzed by simultaneous monitoring of its four activities." *J Biol Chem* 273: 29512-29518). In addition to controlling RNR activity, the allosteric mechanism also regulates the substrate specificity (Jordan, et al. (1998) "Ribonucleotide reductases." *Annu Rev Biochem* 67: 71-98).

RNRs are structurally diverse, and the metal cofactors, e.g., electron donors, they require are, likewise, structurally and chemically diverse. In fact, RNRs can be divided into four classes based on their metal cofactors. Class I rRNRs and generate a stable tyrosyl radical on the protein through activation of O$_2$ by a diferric center. Class I reductases are further divided into class IA and class IB, based upon differences in enzyme regulation. Class IA reductases are distributed in eukaryotes, eubacteria, bacteriophages, and viruses. Class IB reductases are found in eubacteria and can produce radicals using manganese. Class II RNRs, which can function wither in the presence or absence of $O_2$, generate a transient 5'-deoxyadenosyl radical through cleavage of the C—CO bond in adenosylcobalamin (AdoCbl). Class III RNRs are generally anaerobic and generate a stable glycyl radical on the protein by cleavage of S-adenosylmethionine. Class IV RNRs are proposed to comprise a manganese cofactor adjacent to a tyrosyl radical.

Class I RNRs comprise RNR1 and RNR2 subunits, which can associate to form active heterodimeric tetramers. A general mechanistic model for class I RNRs comprises three steps: 1) generation of the tyrosyl radical by the diiron center in subunit R2; 2) radical transfer to generate the proposed thiyl radical near the substrate bound in subunit R1; and 3) catalytic reduction of the bound ribonucleotide. Amino acid- or substrate-derived radicals are involved in all three major reactions. In preferred embodiments of the invention, tyrosine residues in class I RNRs can advantageously be replaced with the unnatural amino acid $NH_2Y$, e.g., to elucidate the mechanistic function of each naturally occurring tyrosine residue in radical propagation. The tyrosine residues that can be replaced, e.g., in an E. coli Class I RNR, using the methods provided by the invention can include ribonucleotide reductase comprising an $NH_2Y$ mutation at one or more of $Y_{730}$, $Y_{731}$, $Y_{122}$, and/or $Y_{356}$ of the $\beta 2$ subunit.

Further details regarding the structure, mechanism, and/or regulation of ribonucleotide reductases can be found in, e.g., Stubbe & van der Donk (1995) "Ribonucleotide reductases: radical enzymes with suicidal tendencies." *Chem Biol* 2: 793-801; Torrents et al. (2002) "Ribonucleotide Reductases: Divergent Evolution of an Ancient Enzyme" *Journal of Molecular Evolution* 55: 138-152; Norlund, et al. (2006) "Ribonucleotide reductases." *Annu Rev Biochem* 75: 681-706; Kolberg, et al. (2004) "Structure, function, and mechanism of ribonucleotide reductases." *Biochim Biophys Acta* 1699: 1-34. Further details regarding the elucidation of the mechanism of radical propagation in a class I RNR are explained in the example below.

Expressing, Purifying and Isolating Reductases Comprising $NH_2Y$ Residues

The nucleic acids of the invention (e.g., nucleic acids derived from reductase nucleic acids that comprise selector codons and, e.g., encode one or more polypeptide chain of a reductase enzyme) can be produced according to standard cloning methods. Procedures for isolating, cloning, and amplifying nucleic acids; and for providing nucleic acid constructs to and expressing nucleic acid constructs in cells and cell free systems are replete in the literature and can be used in the present invention to provide and express a nucleic acid that comprises a selector codon, e.g., to produce a reductase protein, e.g., a class I or class IV ribonucleotide reductase, that comprises an $NH_2Y$ residue. The recombinant reductase enzyme can be derived from any of a variety of sources, including eukaryotes, e.g., humans, mice, yeast and others, prokaryotes, archea, and viruses, e.g., a herpes simplex virus. In preferred embodiments, a nucleic acid of the invention can encode a recombinant E. coli ribonucleotide reductase comprising an $NH_2Y$ mutation at a $Y_{730}$, $Y_{731}$, $Y_{122}$, and/or $Y_{356}$ in the $\alpha 2$ subunit. Alternatively, a nucleic acid of the invention can optionally encode any ribonucleotide reductase included in classes I-IV or any reductase with an EC number between 1.1 and 1.99, as described elsewhere herein.

Further details regarding nucleic acid cloning and expression techniques can be found in Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (3rd Ed.), Vol. 1-3, Cold Spring Harbor Laboratory, Cold Spring Harbor, N.Y., 2000 ("Sambrook"); *The Nucleic Acid Protocols Handbook* Ralph Rapley (ed) (2000) Cold Spring Harbor, Humana Press Inc (Rapley); *Current Protocols in Molecular Biology*, F. M. Ausubel et al., eds., Current Protocols, a joint venture between Greene Publishing Associates, Inc. and John Wiley & Sons, Inc., (supplemented through 2007) ("Ausubel")); *PCR Protocols A Guide to Methods and Applications* (Innis et al. eds) Academic Press Inc. San Diego, Calif. (1990) (Innis); Chen et al. (ed) *PCR Cloning Protocols, Second Edition* (Methods in Molecular Biology, volume 192) Humana Press; in Viljoen et al. (2005) *Molecular Diagnostic PCR Handbook* Springer; and Demidov and Broude (eds) (2005) *DNA Amplification: Current Technologies and Applications*. Horizon Bioscience, Wymondham, UK. Other useful references, e.g., for cell isolation and culture (e.g., for subsequent nucleic acid isolation), include Freshney (1994) *Culture of Animal Cells*, a Manual of Basic Technique, third edition, Wiley-Liss, New York and the references cited therein; Payne et al. (1992) Plant Cell and Tissue Culture in Liquid Systems John Wiley & Sons, Inc. New York, N.Y.; Gamborg and Phillips (eds) (1995) Plant Cell, Tissue and Organ Culture; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

Assessing the mechanistic role of an amino acid, e.g., a tyrosine amino acid, in a reductase enzyme, e.g., an E. coli-derived ribonucleotide reductase, entails the purification of a recombinant reductase in which the natural amino acid of interest has been replaced with an $NH_2Y$ residue. High yields of recombinant reductase can be obtained from cells pastes or extracts, e.g., derived from cells in which a recombinant reductase of the invention has been expressed. A cell paste or extract can comprise, e.g., about 2 mg/g reductase, or, more preferably, 4-6 mg/g recombinant reductase. A variety of protein purification methods are well known in the art and can be applied to the purification and analysis of reductase variants that include at least one $NH_2Y$ residue. These techniques, and others that are necessary for the analysis of polypeptides, include those set forth in R. Scopes, *Protein Purification*, Springer-Verlag, N.Y. (1982); Deutscher, *Methods in Enzymology Vol. 182: Guide to Protein Purification*, Academic Press, Inc. N.Y. (1990); Sandana (1997) *Bioseparation of Proteins*, Academic Press, Inc.; Bollag et al. (1996) *Protein Methods*, 2nd Edition Wiley-Liss, NY; Walker (1996) *The Protein Protocols Handbook* Humana Press, NJ; Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice* 3rd Edition Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ; and the references cited therein.

Further details regarding protocols for expression and isolation of reductase proteins such as E. coli RNR are described in the examples hereinbelow.

Methods of Detecting $NH_2Y$ in Reductase Enzymes

Example 1 below provides details regarding the detection of $NH_2Y$ residues in reductase enzymes, e.g., for detection of $NH_2Y$ residue incorporation and, e.g., as a molecular probe for detecting radical formation. Two common methods that can be used include EPR spectroscopy and spectral analysis, e.g., using UV-vis spectroscopy. These methods are commonly available, and one of skill is familiar with their use in the detection of amino acid residues, radicals, and other moieties of interest.

Electron paramagnetic resonance (EPR), which is also known as electron spin resonance (ESR) and electron magnetic resonance (EMR), is a form of spectroscopy that can be used to detect and identify free radicals and paramagnetic centers. EPR spectroscopy measures the absorption of microwave radiation by an unpaired electron when it is placed in a strong static magnetic field, $B_0$, and exposed to a low-amplitude, high-frequency magnetic field, $B_1$, that is perpendicular to $B_0$. Highly unstable free radicals can, in many cases, be stabilized for EPR characterization by spin trapping. In fact, EPR spin-trapping can be advantageously applied to the detection and analysis of free radical intermediates in generated by metalloproteins, such as certain RNR reductases, as discussed herein.

Relatedly, rapid freeze quench (RFQ) EPR can be used to measure the kinetics of formation and decay of reaction intermediates that are EPR-active, e.g., free radicals. RFQ EPR entails arresting a reaction, e.g., catalyzed by an RNR, by rapid freezing and sustained low temperature after a reaction is allowed to proceed for a specified time. The trapped species are then analyzed by EPR. This method can be beneficially applied to the detection of, e.g., NH2Y radical formation, by a recombinant reductase of the invention. Briefly, in RFQ EPR, the reactants are mixed together rapidly and the reaction carried out for a pre-determined time period, e.g., on the millisecond to second timescale. The reaction is stopped or quenched by squirting the mixture rapidly into, e.g., liquid isopentane that is maintained at $-140°$ C. The crystals formed upon quenching of the reaction are packed into an EPR tube and the EPR spectrum is subsequently acquired to determine the kinetics and structure of the radical that is monitored.

Further details regarding EPR techniques can be found in Weil and Bolton (2007) *Electron Paramagnetic Resonance: Elementary Theory and Practical Applications Second Edition*, Wiley; and in Graslund, et al. (1996) "Electron Paramagnetic Resonance and Nuclear Magnetic Resonance Studies of Class I Ribonucleotide Reductase." *Annu Rev Biophys Biomolec Struct* 25: 259-286. Other resonance methods such as nuclear magnetic resonance (NMR) can also be used to analyze $NH_2Y$ residues in reductase proteins. For a general discussion of NMR techniques, see, e.g., *Introduction to Solid-State NMR Spectroscopy* (2004) Melinda J. Duer (Editor), Wiley.

Other spectroscopic methods, including stopped flow spectroscopy, can also be used, e.g., to acquire kinetic data on the kinetics of free radical formation and/or propagation during, e.g., an RNR-catalyzed reaction. For a discussion of UV-vis spectroscopy and other spectroscopic techniques that can be used to analyze the mechanistic role of $NH_2Y$ residues in reductase proteins, and/or to monitor reductase reaction kinetics, see, e.g., Tong, et al. (1998) "Characterization of Y122F R2 of *Escherichia coli* Ribonucleotide Reductase by Time-Resolved Physical Biochemical Methods and X-ray Crystallography." *Biochem* 37: 5840-5848; Lassman, et al. (2005) "An advanced EPR stopped-flow apparatus based on a dielectric ring resonator." *J Mag Res* 172: 312-323; Pavia (1996) *Introduction to Spectroscopy: A Guide for Students of Organic Chemistry*, Harcourt College Pub; Sorrel (1998) *Interpreting Spectra of Organic Molecules* University Science Books; and Mohan (2007) *Molecular Spectroscopy: An Introduction* ISBN: 978-81-7319-549-5.

Additional Details Regarding Term Definitions

A "reductase enzyme" is an enzyme that catalyses a reduction reaction. Because such enzymes catalyze reactions in either direction, most reductases can, under the proper conditions, behave as a reductase or an oxidase; accordingly, the term oxidoreductase is also used to describe this broad family of structurally diverse enzymes. Examples of reductase enzymes that can be used with the invention include those with Enzyme Commission number (EC number) "EC1". Further details regarding classes of reductases are elaborated elsewhere herein.

Derived from: As used herein, the term "derived from" refers to a component that is isolated from or made using a specified molecule or organism, or information from the specified molecule or organism. For example, a polypeptide that is derived from a second polypeptide can include an amino acid sequence that is identical or substantially similar to the amino acid sequence of the second polypeptide, e.g., other than the incorporation of unnatural amino acids into the second polypeptide. In the case of polypeptides, the derived species can be obtained by, for example, mutagenesis. The mutagenesis used to derive polypeptides can be intentionally directed or intentionally random, or a mixture of each. The mutagenesis of a polypeptide to create a different polypeptide derived from the first can be a random event (e.g., caused by polymerase infidelity) and the identification of the derived polypeptide can be made by appropriate screening methods, e.g., as discussed herein. Mutagenesis of a polypeptide typically entails manipulation of the polynucleotide that encodes the polypeptide.

Derivation of one protein or nucleic acid sequence from another can be identified by detection of homology between the molecules. Two molecules are homologous when they derive from a common ancestral molecule. Homology is ordinarily detected by detecting sequence identity or similarity. The precise cut-off for recognizing homology by assessing sequence identity or similarity varies, but it is common to identify homology when sequence similarity is as low as about 25%. Higher percentages of similarity, e.g., 35%, 45%, 55%, 65%, 75%, 85% 95%, 98% or higher are useful for identifying homology. Sequence similarity/identity can be identified using publicly available programs such as BLASTP (for proteins) and BLASTN (for nucleic acids), e.g., using default parameters (BLASTP and BLASTN are widely available, e.g., from the NCBI, e.g., on the world wide web at ncbi(dot)nlm(dot)nih(dot)gov/blast.

Orthogonal: As used herein, the term "orthogonal" refers to functional molecules, e.g., an orthogonal tRNA (O-tRNA) and/or an orthogonal aminoacyl-tRNA synthetase (O-RS), that function poorly or not at all with endogenous components of a cell, when compared to a corresponding molecule (tRNA or RS) that is endogenous to the cell or translation system. Orthogonal components are usefully provided as cognate components that function well with each other, e.g., an O-RS can be provided that can efficiently aminoacylates a cognate O-tRNA in a cell, even though the O-tRNA functions poorly or not at all as a substrate for the endogenous RS of the cell, and the O-RS functions poorly or not at all with endogenous tRNAs of the cell. Various comparative efficiencies of the orthogonal and endogenous components can be evaluated. For example, an O-tRNA will typically display poor or non-existent activity as a substrate, under typical physiological conditions, with endogenous RSs, e.g., the O-tRNA is less than 10% as efficient as a substrate as endogenous tRNAs for any endogenous RS, and will typically be less than 5%, and usually less than 1% as efficient a substrate. At the same time, the tRNA can be highly efficient as a substrate for the O-RS, e.g., at least 50%, and often 75%, 95%, or even 100% or more as efficient as an aminoacylation substrate as any endogenous tRNA is for its endogenous RS.

Orthogonal aminoacyl-tRNA synthetase: As used herein, an orthogonal aminoacyl-tRNA synthetase (O-RS) is an enzyme that preferentially aminoacylates an O-tRNA with an amino acid in a translation system of interest. The amino acid that the O-RS loads onto the O-tRNA in the present invention is a 3-aminotyrosine ($NH_2Y$)

Orthogonal tRNA: As used herein, an orthogonal tRNA (O-tRNA) is a tRNA that is orthogonal to a translation system of interest. The O-tRNA can exist charged with, e.g., a 3-aminotyrosine, or can exist in an uncharged state. It is also to be understood that an O-tRNA is optionally charged (aminoacylated) by a cognate orthogonal aminoacyl-tRNA synthetase with a 3-aminotyrosine. Indeed, it will be appreciated that the O-tRNA described herein is used to insert a 3-aminotyrosine into a growing polypeptide, during translation, in response to a selector codon.

Cognate: The term "cognate" refers to components that function together, e.g., an orthogonal tRNA and an orthogonal aminoacyl-tRNA synthetase. The components can also be referred to as being complementary.

Preferentially aminoacylates: As used herein in reference to orthogonal translation systems, an O-RS "preferentially aminoacylates" a cognate O-tRNA when the O-RS charges the O-tRNA with 3-aminotyrosine more efficiently than it charges any endogenous tRNA in an expression system. That is, when the O-tRNA and any given endogenous tRNA are present in a translation system in approximately equal molar ratios, the O-RS will charge the O-tRNA more frequently than it will charge the endogenous tRNA. Preferably, the relative ratio of O-tRNA charged by the O-RS to endogenous tRNA charged by the O-RS is high, preferably resulting in the O-RS charging the O-tRNA exclusively, or nearly exclusively, when the O-tRNA and endogenous tRNA are present in equal molar concentrations in the translation system. The relative ratio between O-tRNA and endogenous tRNA that is charged by the O-RS, when the O-tRNA and O-RS are present at equal molar concentrations, is greater than 1:1, preferably at least about 2:1, more preferably 5:1, still more preferably 10:1, yet more preferably 20:1, still more preferably 50:1, yet more preferably 75:1, still more preferably 95:1, 98:1, 99:1, 100:1, 500:1, 1,000:1, 5,000:1 or higher. The O-RS "preferentially aminoacylates an O-tRNA with a 3-aminotyrosine" when (a) the O-RS preferentially aminoacylates the O-tRNA compared to an endogenous tRNA, and (b) where that aminoacylation is specific for the 3-aminotyrosine, as compared to aminoacylation of the O-tRNA by the O-RS with any natural amino acid. For example, when a 3-aminotyrosine and natural amino acids are present in equal molar amounts in a translation system comprising a relevant O-RS of the sequence listing herein and a relevant O-tRNA of the sequence listing herein, the O-RS will load the O-tRNA with 3-aminotyrosine more frequently than with any natural amino acid. Preferably, the relative ratio of O-tRNA charged with 3-aminotyrosine to O-tRNA charged with the natural amino acid is high. More preferably, O-RS charges the O-tRNA exclusively, or nearly exclusively, with the 3-aminotyrosine. The relative ratio between charging of the O-tRNA with the 3-aminotyrosine and charging of the O-tRNA with a natural amino acid, when both the natural amino acid and 3-aminotyrosine are present in the translation system in equal molar concentrations, is greater than 1:1, preferably at least about 2:1, more preferably 5:1, still more preferably 10:1, yet more preferably 20:1, still more preferably 50:1, yet more preferably 75:1, still more preferably 95:1, 98:1, 99:1, 100:1, 500:1, 1,000:1, 5,000:1 or higher.

Selector codon: The term "selector codon" refers to codons recognized by the O-tRNA in the translation process and not recognized by an endogenous tRNA. The O-tRNA anticodon loop recognizes the selector codon on the mRNA and incorporates the amino acid with which it is charged, e.g., 3-aminotyrosine, at this site in the polypeptide. Selector codons can include, e.g., nonsense codons, such as, stop codons, e.g., amber, ochre, and opal codons; four or more base codons; rare codons; noncoding codons; and codons derived from natural or unnatural base pairs and/or the like.

Suppression activity: As used herein, the term "suppression activity" refers, in general, to the ability of a tRNA, e.g., a suppressor tRNA, to allow translational read-through of a codon, e.g., a selector codon that is an amber codon or a 4-or-more base codon, that would otherwise result in the termination of translation or mistranslation, e.g., frame-shifting. Suppression activity of a suppressor tRNA can be expressed as a percentage of translational read-through activity observed compared to a second suppressor tRNA, or as compared to a control system, e.g., a control system lacking an O-RS.

Suppressor tRNA: A suppressor tRNA is a tRNA that alters the reading of a messenger RNA (mRNA) in a given translation system, typically by allowing the incorporation of an amino acid in response to a stop codon (i.e., "read-through") during the translation of a polypeptide. In some aspects, a selector codon of the invention is a suppressor codon, e.g., a stop codon, e.g., an amber, ocher or opal codon, a four base codon, a rare codon, etc.

Translation system: The term "translation system" refers to the components that incorporate an amino acid into a growing polypeptide chain (protein). Components of a translation system can include, e.g., ribosomes, tRNAs, synthetases, mRNA and the like. The O-tRNA and/or the O-RSs of the invention can be added to or be part of an in vitro or in vivo translation system, e.g., in a non-eukaryotic cell, e.g., a bacterium, such as *E. coli*, or in a eukaryotic cell, e.g., a yeast cell, a mammalian cell, a plant cell, an algae cell, a fungus cell, an insect cell, and/or the like.

Unnatural amino acid: As used herein, the term "unnatural amino acid" refers to any amino acid, modified amino acid, and/or amino acid analogue, that is not one of the 20 common naturally occurring amino acids. For example, the unnatural amino acid 3-aminotyrosine finds use with the invention.

EXAMPLES

Example 1

Site Specific Insertion of 3-Aminotyrosine into Subunit α2 of *E. Coli* Ribonucleotide Reductase: Direct Evidence for Involvement of $Y_{730}$ and $Y_{731}$ in Radical Propagation

*E. coli* ribonucleotide reductase (RNR) catalyzes the production of deoxynucleotides using complex radical chemistry. Active RNR is composed of a 1:1 complex of two subunits: α2 and β2. α2 binds nucleoside diphosphate substrates and deoxynucleotide/ATP allosteric effectors and is the site of nucleotide reduction. β2 contains the stable diiron tyrosyl radical ($Y_{122}$.) cofactor that initiates deoxynucleotide formation. This process is proposed to involve reversible radical transfer over >35 Å between the $Y_{122}$. in β2 and $C_{439}$ in the active site of α2. A docking model of α2β2, based on structures of the individual subunits, suggests that radical initiation involves a pathway of transient, aromatic amino acid radical intermediates, including $Y_{730}$ and $Y_{731}$ in α2. In this study the function of residues $Y_{730}$ and $Y_{731}$ is investigated by their site-specific replacement with 3-aminotyrosine ($NH_2Y$). Using the in vivo suppressor tRNA/aminoacyl-tRNA synthetase method, $Y_{730}NH_2Y$-α2 and $Y_{731}NH_2Y$-α2 have been generated with high fidelity in yields of 4-6 mg/g of cell paste. These mutants have been examined by stopped flow UV-vis and EPR spectroscopies in the presence of β2, CDP and ATP. The results reveal formation of an $NH_2Y$ radical ($NH_2Y_{730}$· or $NH_2Y_{731}$·) in a kinetically competent fashion. Activity assays demonstrate that both $NH_2Y$-α2s make deoxynucleotides. These results show that the $NH_2Y$· can oxidize $C_{439}$ suggesting a hydrogen atom transfer mechanism for the radical propagation pathway within α2. The observed $NH_2Y$· may constitute the first detection of an amino acid radical intermediate in the proposed radical propagation pathway during turnover.

Introduction

In all organisms, ribonucleotide reductases (RNRs) catalyze the conversion of nucleotides to 2'-deoxynucleotides, providing the precursors required for DNA biosynthesis and repair.[1-3] The mechanism of nucleotide reduction is conserved in all RNRs and requires formation of a transient active site thiyl radical ($C_{439}$·, E. coli RNR numbering used throughout the text).[4,5] However, the mechanism of active site thiyl radical generation, the radical initiation event, is not conserved and provides the basis for distinction between four classes of RNRs.[6-9] A major unresolved mechanistic issue is that of thiyl radical formation in class I RNRs, and presumably in the recently identified class IV RNR. In this paper, we report site-specific incorporation of 3-aminotyrosine ($NH_2Y$) into one of the subunits of E. coli RNR and present the insights provided by these mutants into the mechanism of radical initiation.

The E. coli class I RNR consists of two homodimeric subunits, α2 and β2, which form an active 1:1 complex during turnover.[10-12] α2 is the business end of the complex. It contains the active site where thiyl radical-mediated nucleotide reduction occurs, as well as multiple allosteric effector binding sites which modulate substrate specificity and turnover rate.[13] β2 houses the stable diferric tyrosyl radical ($Y_{122}$·)[14-16] cofactor which is required for formation of the transient $C_{439}$· in the active site of α2.[4-6] The structure of α2[6,17] and β2[18,19] have been solved and a structure containing both subunits has also been reported.[20] A structure of the active α2β2 complex, however, has remained elusive. From the individual structures of α2 and β2, Uhlin and Eklund have generated a docking model of the α2β2 complex based on shape and charge complementarities and conserved residues.[6] This model suggests that the $Y_{122}$· in β2 is located >35 Å away from $C_{439}$ in α2 (FIG. 1).[21-23] Radical propagation over this long distance requires the involvement of transient amino acid intermediates.[24-26] The residues proposed to participate in this pathway are universally conserved in all class I RNRs.

Evidence in support of the long distance between $Y_{122}$· and $C_{439}$ has recently been obtained from pulsed electron-electron double resonance spectroscopic measurements[27] with a mechanism based inhibitor.[28-32] The distance obtained from this study is consistent with the docking model and establishes that a large conformational change, that positions $Y_{122}$· in β2 adjacent to $C_{439}$ in α2, does not occur.[32]

To examine the validity of the proposed pathway, site-directed mutagenesis[33,34] and complementation studies[35] have been carried out. These studies demonstrate that each residue in FIG. 1 plays an important role in RNR function. However, the absence of activity in these mutants precludes mechanistic investigations.[33,34]

At present, evidence for the involvement of only one of the proposed pathway residues, $Y_{356}$, is substantial. Demonstration of the involvement of this residue is particularly important as it resides within a disordered region of β2 and hence its distance to $W_{48}$ in β2 and to $Y_{731}$ in α2 is long and not known (FIG. 1). We have recently been able incorporate unnatural amino acids at residue 356 using expressed protein ligation methods, to generate mechanistically informative mutants.[36,37] In one variant, $Y_{356}$ was replaced with the radical trap 3,4-dihydroxyphenylalanine (DOPA).[38] Studies with $DOPA_{356}$-β2 and α2 in the presence of substrate and/or effector showed formation of a DOPA radical (DOPA·) in a kinetically competent fashion directly demonstrating that residue 356 is redox-active.[38] We have also employed a DOPA heterodimer, DOPA-ββ' (where the β'-monomer lacks the C-terminal 22 residues), to show reverse hole migration from residue 356 to $Y_{122}$·.[39] The most compelling evidence, however, for the redox-active role of $Y_{356}$ has come from a series of semisynthetic $F_nY_{356}$-β2s in which fluorotyrosine analogues ($F_nY$s, n=2, 3, or 4) were site-specifically inserted at this residue.[40-43] These $F_nY_{356}$-β2 derivatives have allowed systematic modulation of the reduction potential and $pK_a$ of this residue, key to unraveling the role of proton-coupled electron transfer within the pathway.[21,40] Activity assays of $F_nY_{356}$-β2s showed that radical initiation, and thus nucleotide reduction, is turned on or off based on the reduction potential difference between the $F_nY$ and Y.[43] In addition, modulation of the $pK_a$ in $F_nY$-β2s, allowed us to show that there was no obligate coupling between the electron and proton at this residue during radical transport.[43] Studies using semi-synthetic β2s have thus defined the function and mechanism of residue 356 in radical propagation.

In contrast, the roles of α2 residues $Y_{730}$ and $Y_{731}$ in radical propagation are still ill-defined. Mutagenesis studies have demonstrated their importance in RNR function.[34,44,45] However, as with residue $Y_{356}$ in β2, the inactivity of these mutants ($Y_{730}F$-α2 and $Y_{731}F$-α2) precluded mechanistic interrogation of the role of $Y_{730}$ and $Y_{731}$ in radical propagation. Furthermore, incorporation of unnatural amino acids into α2 is not feasible by expressed protein ligation given the location of these residues. We have thus sought an alternative method to site-specifically incorporate unnatural amino acids.

We now report evolution of an $NH_2Y$-specific Methanococcus jannaschii aminoacyl-tRNA synthetase ($NH_2Y$-RS) and its use in vivo with the appropriate M. jannaschii amber suppressor tRNA, to incorporate $NH_2Y$ at residues $Y_{730}$ and $Y_{731}$ of the α2 subunit.[46-50] $NH_2Y$ was chosen as a probe because its reduction potential (0.64 V at pH 7.0, see FIG. 1, Scheme 1)[51] is 0.19 V lower than that of Y, indicating that it might act as a radical trap, similar to DOPA, and directly report on participation of residues $Y_{730}$ and $Y_{731}$ in hole migration (FIG. 1). Furthermore $NH_2Y$ is more stable to oxidation than DOPA, making it a more practical target.[51,52] Using this methodology, 100 mg quantities of each $NH_2Y$-α2 has been generated. Incubation of $Y_{730}NH_2Y$-α2 (or $Y_{731}NH_2Y$-α2) with β2, substrate and allosteric effector, results in formation of an $NH_2Y$ radical ($NH_2Y$·) in a kinetically competent fashion as demonstrated by stopped-flow (SF) UV-vis and EPR spectroscopy. The $NH_2Y$-α2s retain the ability to make deoxynucleotides, suggesting that the $NH_2Y$· observed, occurs during radical propagation in a complex that is competent in nucleotide reduction. These results suggest that direct hydrogen atom transfer is the operative mechanism for hole migration within α2.

Materials And Methods

Materials. Luria Bertani (LB) medium, BactoAgar, 2YT medium, and small and large diameter (100 and 150 mm) Petri dish plates were obtained from Becton-Dickinson. $NH_2Y$, M9 salts, tetracycline (Tet), kanamycin (Kan), ampicillin (Amp), L-arabinose (L-Ara), chloramphenicol (Cm), L-leucine (Leu), D-biotin, thiamine HCl, ATP, cytidine-5'-diphosphate (CDP), NADPH, ethylenediamine tetraacetic acid (EDTA), glycerol, Bradford Reagent, Sephadex G-25, phenylmethanesulfonyl fluoride (PMSF), streptomycin sulfate, hydroxyurea, 2'-deoxycytidine and 2'-deoxyguanidine-5'-triphosphate (dGTP) were purchased from Sigma-Aldrich. Isopropyl-β-D-thiogalactopyranoside (IPTG), DL-dithiothreitol (DTT) and T4 DNA ligase were from Promega. DH10B competent cells and oligonucleotides were from Invitrogen. Site-directed mutagenesis was carried out with the Quickchange Kit from Stratagene. Calf-intestine alkaline phosphatase (CAP, 20 U/μL) was from Roche. KpnI and XboI restriction enzymes were from NEB. The pTrc vector was a generous gift of Prof. Sinskey (Department of Biology, M. I. T.). The purification of $E.$ $coli$ thioredoxin[53] (TR, 40 units/mg), $E.$ $coli$ thioredoxin reductase[54] (TRR, 1400 units/mg), and wt β2[55] (6200-7200 nmol/min·mg, 1-1.2 radicals per dimer) have been described. The concentrations of α2, $Y_{730}NH_2Y$-α2 and $Y_{731}NH_2Y$-α2 were determined using $\epsilon_{280\ nm}=189\ nM^{-1}cm^{-1}$. Glycerol minimal media leucine (GMML) contains final concentrations of 1% (v/v) glycerol, 1×M9 salts, 0.05% (w/v) NaCl, 1 mM $MgSO_4$, 0.1 mM $CaCl_2$ and 0.3 mM L-leucine. RNR assay buffer consists of 50 mM Hepes, 15 mM $MgSO_4$, 1 mM EDTA, pH 7.6.

Qualitative assay for cellular uptake of $NH_2Y$ by LC-MS. The uptake assay was performed as previously described with minor modifications.[48] DH10B $E.$ $coli$ cells were grown to saturation at 37° C. in GMML in the presence of 1 mM $NH_2Y$ and 0.1 mM DTT and subsequently harvested and lysed as outlined previously. Chromatography of the crude extract was performed on a Zorbax SB-C18 (5 μm, 4.6×150 mm) column with a linear gradient from 5% to 25% MeCN in 0.1% TFA solution over 8 min at 0.5 mL/min. Under these conditions, $NH_2Y$ elutes at ~13% MeCN. For HPLC-ESI-MS analysis, $NH_2Y$ standard solutions were prepared in water.

Directed Evolution of $NH_2Y$-RS in $E.$ $coli$. Positive and negative selection cycles were carried out as detailed previously.[48] Briefly, plasmid pBK-JYRS encodes a library of $M.$ $jannaschii$ TyrRS variants, which are randomized at 6 residues within 6.5 Å of the Tyr binding cleft, under the control of the $E.$ $coli$ GlnRS promoter and contains a $Kan^R$ marker.[46] Plasmid pREP/YC-J17 was used for positive selections;[56] it encodes a chloramphenicol acetyl transferase (CAT) gene with a nonessential amber mutation, $Asp_{112}TAG$, and a T7 RNA polymerase (T7 RNAP) gene with two nonessential amber mutations, $Met_1TAG$ and $Gln_{107}TAG$. It also contains a gene for the cognate mutant $tRNA_{CUA}$ ($mutRNA_{CUA}$) that is charged by the library of TyrRSs, a GFPuv gene, the expression of which is driven by T7 RNAP and a $Tet^R$ marker. Plasmid pLWJ17B3 was used for negative selections;[57,58] it encodes a toxic barnase gene with three nonessential amber mutations, $Gln_2TAG$, $Asp_{44}TAG$ and $Gly_{65}TAG$, under the control of an Ara promoter. It also contains the $mutRNA_{CUA}$ gene and an $Amp^R$ marker (Table 1).

In each positive selection round, the pBK-JYRS plasmid library, containing the library of mutant TyrRSs, was transformed into $E.$ $coli$ DH10B competent cells containing plasmid pREP/YC-J17 by electroporation.[48] The cells were recovered in SOC medium and grown at 37° C. for 1 h. They were then washed twice with GMML and plated onto 6-8 GMML agar plates (150 mm) containing 12 μg/mL Tet, 25 μg/mL Kan, 60 μg/mL chloramphenicol (Cm), 1 mM $NH_2Y$, and 100 μM DTT. DTT was included in all solutions or plates that contained $NH_2Y$ in order to maintain a reducing environment. Plates were incubated at 37° C. for 72 h. Surviving cells were scraped from the plates and pooled into GMML liquid medium. The cells were then subjected to plasmid isolation using the Qiagen Miniprep Kit. The pBK-JYRS library (~3 kb) was separated from pREP/YC-J17 (~10 kb) by agarose gel electrophoresis and extracted from the gel with the Qiagen Gel Extraction Kit. Plasmid DNA was quantitated using $OD_{260\ nm}$.

To perform a negative selection, plasmid DNA isolated from the positive selection was transformed by electroporation into $E.$ $coli$ DH10B competent cells containing pLWJ17B3.[48] The cells were recovered in SOC medium, shaken at 37° C. for 1 h and plated onto LB agar plates containing 100 μg/mL Amp, 50 μg/mL Kan and 0.2% L-Ara. The plates were incubated at 37° C. for 10-12 h. Surviving cells were recovered and plasmid isolation was performed as described above.

After a total of 6 rounds (3 positive and 3 negative selections), the $4^{th}$ positive selection was performed by spreading cells onto two sets of plates. One set contained $NH_2Y$/DTT as described for the positive rounds, the other contained only DTT. The two sets of plates were examined for differences in green fluorescence stemming from GFPuv, the expression of which is driven by T7 RNAP on the positive selection plasmid (Table 1). A total of 48 single colonies were selected from the plates which contained $NH_2Y$/DTT and inoculated into 100 μL GMML in a 96 well plate. One μL from each resulting cell suspension was plated onto two sets of GMML agar plates containing 0, 20, 40, 60, 80 and 110 μg/mL Cm and 0.1 mM DTT in the presence and absence of 1 mM $NH_2Y$. Plates were incubated at 37° C. for 72-120 h. Candidate clones are able to survive on plates with $NH_2Y$/DTT and high concentrations of Cm (~100 μg/mL) and emit green fluorescence under UV light, but die on plates without $NH_2Y$ at low concentration of Cm (20 μg/mL). Candidate clones were inoculated into 5 mL 2YT medium containing 24 μg/mL Tet and 50 μg/mL Kan and grown to saturation. Plasmid DNA was then isolated as described above and analyzed by DNA sequencing. The plasmid containing the $NH_2Y$-RS gene, which was selected by the procedures above, is pBK-$NH_2Y$-RS.

Expression of $K_7NH_2Y$—Z-domain. The efficiency of $NH_2Y$ incorporation using pBK-$NH_2Y$-RS was tested using the C-terminally His-tagged Z-domain of protein A (Z-domain), as previously described.[48] $LEIZ^{57,59}$, which encodes the Z-domain with an amber stop codon at residue 7 and $mutRNA_{CUA}$, and pBK-$NH_2Y$-RS were cotransformed into BL21(DE3) competent cells. All growths were carried out in the presence of Kan (50 μg/mL) and Cm (35 μg/mL) at 37° C. A single colony was inoculated into a 5 mL 2YT medium and grown to saturation (~13 h). One mL of this saturated culture was diluted into 25 mL 2YT medium and grown to saturation overnight (~11 h). Ten mL of this culture were then diluted into each of 2×250 mL GMML medium. When the $OD_{600\ nm}$ reached 0.65 (9 h), one of the cultures was supplemented with $NH_2Y$ and DTT (final concentrations of 1 mM and 0.1 mM, respectively); the other culture was supplemented only with DTT (0.1 mM). Fifteen min after addition of $NH_2Y$/DTT (or DTT), IPTG was added to each culture to a final concentration of 1 mM. After 5 h, cells were harvested by centrifugation. Z-domain grown in the presence and absence of $NH_2Y$ was then purified by $Ni^{2+}$ affinity chromatography, as previously described, and subjected to SDS PAGE and MALDI-TOF MS analysis.[48] For MALDI-TOF MS analysis, the Z-domain was exchanged into water by dialysis and mass spectra were subsequently obtained under positive ionization mode at the Scripps Center for Mass Spectrometry.

Cloning of pTrc-nrdA. To generate vector pTrc-nrdA, the nrdA gene was amplified with primers 1, e.g., SEQ ID NO: 1, (5'-AT AAT TGGTACCCA AAA ACA GGT ACG ACA TAC ATG AAT C-3') and 2, e.g., SEQ ID NO: 2, (5'-GCT GCA GGT CGA CTCTAGAGG ATC CCC CCT TCT TAT C-3') using Pfu Turbo polymerase. The primers contain KpnI and XboI cut sites at the 5' and 3' ends of the gene (underlined), respectively. The fragment was purified using the PCR Purification Kit from Qiagen. The isolated DNA was then incubated with KpnI and XboI, the resulting products separated on an agarose gel, and extracted with the Qiagen Gel Extraction Kit. The gene fragment was ligated into pTrc, which had been cut with the same restriction enzymes. Incubation of the insert-vector in a ratio of 3:1 and ligation with T4 DNA ligase at 16° C. for 30 min resulted in pTrc-nrdA.

Expression of wt α2 from vector pTrc-nrdA was performed in BL21(DE3) cells as previously described for expression from plasmid pMJ1-nrdA and yielded 3 g of wet cell paste per L culture.[55,62] Purification of α2 (see below) yielded 10 mg of α2 per g of wet cell paste with >95% purity and a specific activity of 2500 nmol/min·mg as measured by the spectrophotometric RNR assay (see below).

Generation of pTrc-nrdA$_{730}$TAG and pTrc-nrdA$_{731}$TAG. The TAG codon was inserted into position 730 or 731 of the nrdA gene in vector pMJ1-nrdA using the Stratagene Quickchange Kit. Primers 3, e.g., SEQ ID NO: 3, (5'-G GTC AAA ACA CTG TAG TAT CAG AAC ACC CG-3') and 4, SEQ ID NO: 4, (5'-CG GGT GTT CTG ATA CTA CAG TGT TTT GAC C-3') were used for incorporation of TAG into position 730 of α2. Primers 5, e.g., SEQ ID NO: 5, (5'-G GTC AAA ACA CTG TAT TAG CAG AAC ACC CG-3') and 6, e.g., SEQ ID NO: 6, (5'-CG GGT GTT CTG CTA ATA CAG TGT TTT GAC C-3') were used for incorporation of TAG into position 731 of α2. The mutations were confirmed by sequencing the entire gene at the MIT Biopolymers Laboratory. The nrdA$_{730}$TAG and nrdA$_{731}$TAG genes were then amplified with primers 1 and 2 and ligated into vector pTrc as described above for wt nrdA.

Cloning of pAC-NH$_2$Y-RS. The pAC vector is analogous to vector pSup, which has been described, except that it contains the Tet$^R$ selection marker rather than the Cm$^R$ marker.[63] In addition, pAC-NH$_2$Y-RS contains the NH$_2$Y-RS gene under control of glnS' promoter and rrnB terminator and six copies of the mutRNA$_{CUA}$ gene under control of a proK promoter and terminator. To generate pAC-NH$_2$Y-RS, the NH$_2$Y-RS gene was subcloned into the pAC vector from pBK-NH$_2$Y-RS using the PstI and NdeI restriction sites, which are 3' and 5' of the NH$_2$Y-RS gene, respectively.

Expression of Y$_{730}$NH$_2$Y-α2 and Y$_{731}$NH$_2$Y-α2. Successful expression of Y$_{730}$NH$_2$Y-α2 was achieved with the pTrc-nrdA$_{730}$TAG/pAC-NH$_2$Y-RS expression system, where vector pTrc-nrdA$_{730}$TAG contains the nrdA gene with an amber codon at position 730 under control of the trp/lac (trc) promoter and rrnB terminator and an Amp$^R$ marker. E. coli DH10B cells were transformed with vectors pTrc-nrdA$_{730}$TAG and pAC-NH$_2$Y-RS, and grown at 37° C. on LB/Agar plates containing Amp (100 µg/mL) and Tet (25 µg/mL) for two days. All liquid culture growths contained Amp (100 µg/mL) and Tet (25 µg/mL) and were carried out in a shaker/incubator at 37° C. and 200 rpm. A single colony from the plate was inoculated into 5 mL of 2YT medium and grown to saturation (~2 days). The 5 mL saturated culture was then diluted into 180 mL of 2YT medium and grown to saturation (~1 day). Twenty five mL of this culture were then inoculated into each of 6×6 L Erlenmeyer flasks, each containing 1 L of GMML medium supplemented with D-biotin (1 µg/mL), thiamine (1 µg/mL) and a 1× heavy metal stock solution. A 1000× heavy metal stock solution contains the following per L as described:[64] 500 mg MoNa$_2$O$_4$.2H$_2$O, 250 mg CoCl$_2$, 175 mg CuSO$_4$.5H$_2$O, 1 g MnSO$_4$.H$_2$O, 8.75 g MgSO$_4$.7H$_2$O, 1.25 g ZnSO$_4$.7H$_2$O, 1.25 g FeCl$_2$.4H$_2$O, 2.5 g CaCl$_2$.2H$_2$O, 1 g H$_3$BO$_3$ and 1 M HCl. When OD$_{600}$ reached 0.6 (12-18 h), NH$_2$Y and DTT were added to final concentrations of 1 mM and 0.1 mM, respectively. After 15 min, IPTG was added to a final concentration of 1 mM and the growth continued for 4.5 h, at which point the cells were harvested by centrifugation, frozen in liquid N$_2$ and stored at −80° C. Typically, 1.5 g of wet cell paste were obtained per L culture. Expression of Y$_{731}$NH$_2$Y-α2 was carried out in identical fashion using vectors pTrc-nrdA$_{731}$TAG and pAC-NH$_2$Y-RS.

Purification of Y$_{730}$NH$_2$Y-α2 and Y$_{731}$NH$_2$Y-α2. NH$_2$Y-α2s were typically purified from 10 g of wet cell paste. All purification steps were performed at 4° C. Each g of wet cell paste was resuspended in 5 mL of α2 Buffer (50 mM Tris, 1 mM EDTA, pH 7.6) supplemented with 1 mM PMSF and 5 mM DTT. The cells were lysed by passage through a French Pressure cell operating at 14,000 psi. After removal of cell debris by centrifugation (15,000×g, 35 min, 4° C.), DNA was precipitated by dropwise addition of 0.2 volumes of α2 Buffer containing 8% (w/v) streptomycin sulfate. The mixture was stirred for an additional 15 min and the precipitated DNA was removed by centrifugation (15,000×g, 35 min, 4° C.). Then, 3.9 g of solid (NH$_4$)$_2$SO$_4$ was added per 10 mL of supernatant over 15 min (66% saturation). The solution was stirred for an additional 30 min and the precipitated protein isolated by centrifugation (15,000×g, 45 min, 4° C.). The pellet was re-dissolved in a minimal volume of α2 Buffer and desalted using a Sephadex G-25 column (1.5×25 cm, 45 mL). The desalted protein was loaded at a flow rate of 0.5 mL/min directly onto a dATP column (1.5×4 cm, 6 mL), which had been equilibrated in α2 Buffer. The column was washed with 10 column volumes of α2 Buffer. NH$_2$Y-α2 was then eluted in 3-4 column volumes of α2 Buffer containing 10 mM of ATP, 15 mM MgSO$_4$ and 10 mM DTT. ATP was subsequently removed by Sephadex G-25 chromatography. The protein was flash-frozen in small aliquots in liquid N$_2$ and stored at −80° C. Typically 4-6 mg of pure NH$_2$Y-α2 were obtained per g of wet cell paste.

Reaction of NH$_2$Y-α2 with β2, CDP, and ATP monitored by EPR spectroscopy. Pre-reduced wt-α2 or NH$_2$Y-α2s were generated by incubating each variant (40 µM) with 35 mM DTT at room temperature for 40 min. Hydroxyurea and additional DTT were added to final concentrations of 15 mM, and the incubation continued at room temperature for an additional 20 min. Each protein was then desalted on a Sephadex G-25 column (1.5×25 cm, 45 mL), which had been equilibrated in assay buffer (see Materials).

Pre-reduced NH$_2$Y-α2 and ATP were mixed with wt β2 and CDP in assay buffer to give final concentrations 20-24 µM, 3 mM, 20-24 µM and 1 mM, respectively. The reaction was hand-quenched in liquid N$_2$ from 10 s to 12 min. EPR spectra were recorded at 77 K in the Department of Chemistry Instrumentation Facility on a Bruker ESP-300 X-band spectrometer equipped with a quartz finger dewar filled with liquid N$_2$. EPR parameters were as follows: microwave frequency=9.34 GHz, power=30 µW, modulation amplitude=1.5 G, modulation frequency=100 kHz, time constant=5.12 ms, scan time=41.9 s. Analysis of the resulting spectra was carried out using WinEPR (Bruker) and an in-house written program in Excel. These programs facilitate fractional subtraction of the unreacted Y$_{122}$· signal from the recorded spectrum, yielding the spectrum of NH$_2$Y·-α2. The ratio Y· and NH$_2$Y· signals was assessed by comparing the double integral intensity of each trace. EPR spin quantitation was carried out using Cu$^{II}$ as standard.[65]

Kinetics of NH$_2$Y.-α2 formation with β2, CDP and ATP by Stopped-Flow (SF) UV-vis Spectroscopy. SF kinetics was performed on an Applied Photophysics DX. 17MV instrument equipped with the Pro-Data upgrade using PMT detection at λs indicated in figure legends. The temperature was maintained at 25° C. with a Lauda RE106 circulating water bath. Pre-reduced Y$_{730}$NH$_2$Y-α2 (or Y$_{731}$NH$_2$Y-α2) and ATP in one syringe were mixed in a 1:1 ratio with wt β2 and CDP from a second syringe to yield final concentrations of 8-10 µM, 3 mM, 8-10 µM and 1 mM, respectively, in assay buffer. Data were collected in split time-base mode. Time courses shown are the average of at least 6 individual traces. For point-by-point reconstruction of the Y$_{730}$NH$_2$Y.-α2 and Y$_{731}$NH$_2$Y.-α2 absorption profiles, 2-4 traces were averaged between 305 and 365 nm in 5 nm intervals. The absorption change was corrected for the absorption of Y$_{122}$. in this region, based on the published ε at these λs,[66-68] and then plotted against λ. Calculation of the ε for Y$_{730}$NH$_2$Y.-α2 (10500 M$^{-1}$ cm$^{-1}$) and Y$_{731}$NH$_2$Y.-α2 (11000 M$^{-1}$cm$^{-1}$) were performed using the ε of Y$_{122}$. (ε$_{410}$=3700 M$^{-1}$cm$^{-1}$)[68] and assuming that consumption of each mole of Y$_{122}$. leads to formation of one mole of NH$_2$Y. in α2. Curve fitting was performed with OriginPro or KaleidaGraph Software.

Spectrophotometric and radioactive activity assays for RNR. The spectrophoto-metric and radioactive RNR assays were performed as described before.[36,43] The concentration of NH$_2$Y-α2 was 0.2, 1 or 3 µM; β2 was present at a 5-fold molar excess. [5-$^3$H]-CDP (1190 cpm/nmol) was used in the radioactive assay.

Reaction of NH$_2$Y-α2 with β2, N$_3$ADP and dGTP monitored by EPR Spectroscopy. 2'-Azido-2'-deoxyadenosine-5'-diphosphate (N$_3$ADP) was previously prepared by Scott Salowe.[62] Pre-reduced Y$_{730}$NH$_2$Y-α2 (Y$_{731}$NH$_2$Y-α2 or wt α2) and dGTP were mixed with wt β2 and N$_3$ADP in assay buffer to yield final concentrations of 20 µM, 1 mM, 20 µM and 250 µM, respectively. The reaction was hand-quenched in liquid N$_2$ after 20 s. EPR data acquisition and spin quantitation with Cu$^{II}$ were performed as described above. The resulting spectra were analyzed using WinEPR (Bruker) and an in-house written Excel program. Deconvolution of the three signals observed in these experiments was performed by first subtracting the N. signal which has been reported and was reproduced here with the wt α2/β2 reaction. Then, unreacted Y$_{122}$. was subtracted from this spectrum, yielding the NH$_2$Y.-α2 spectrum. The ratio of the three signals was assessed by comparing the double integral intensity of each trace.

Results

Toxicity and uptake of NH$_2$Y. Evolution of an NH$_2$Y-specific aminoacyl-tRNA synthetase (RS) requires that NH$_2$Y is taken up by *E. coli*, that it is not toxic, and that it is not incorporated into proteins by any endogenous RSs. All three requirements were met by NH$_2$Y. When DH10B *E. coli* cells were grown in liquid GMML medium in the presence of NH$_2$Y (1 mM) or NH$_2$Y and DTT (1 mM and 0.1 mM, respectively), NH$_2$Y was observed in all cell extracts as judged by HPLC and ESI-MS.[48] Toxicity of NH$_2$Y was assessed by growing DH10B *E. coli* cells in liquid GMML medium and on Agar plates in the presence of NH$_2$Y or NH$_2$Y/DTT. Growth rates were not significantly affected by the presence of NH$_2$Y. The presence of DTT however, caused cells to grow at a rate 25-35% more slowly than those in the presence of only NH$_2$Y or absence of NH$_2$Y/DTT.

Evolution of an NH$_2$Y-specific RS. The Schultz lab has developed a robust in vivo method for incorporation of unnatural amino acids into any target protein.[46-50] In this method, the RS is selected from a library of *M. jannaschii* TyrRS mutants. A cognate amber suppressor *M. jannaschii* tRNA, mutRNA$_{CUA}$, does not require modification as the region of interaction between mutRNA$_{CUA}$ and the RSs in the library is not varied.[69] Iterative rounds of positive and negative selections are carried out on the RS library which has been randomized at six residues in and around the Y binding cleft: Tyr32, Leu65, Phe108, Gln109, Asp158 and Leu162. The positive selection is based on suppression of an amber stop codon at a permissive site in the CAT gene in the presence of NH$_2$Y/DTT and the cognate tRNA (Table 1).[46] Surviving clones carry RSs that are functional with the host cell translation machinery and incorporate NH$_2$Y or other amino acids in response to the amber stop codon. The negative selection is based on lack of suppression of three amber codons in the toxic barnase gene in the absence of NH$_2$Y (Table 1).[70] Surviving clones carry RSs that do not incorporate any natural amino acids in response to the amber stop codon.

After seven selection cycles, 48 colonies were examined for their ability to suppress the amber stop codon. Single colonies containing pBK-NH$_2$Y-RS and pREP/YC-J17 were picked from the last positive selection (7$^{th}$ round) and plated on GMML agar containing variable concentrations of Cm (0-110 µg/mL) in the presence or absence of NH$_2$Y. Ability to grow with NH$_2$Y/DTT indicates that the amber codon in the CAT gene is suppressed by incorporation of NH$_2$Y. Further, the amber codon in the T7 RNAP gene is suppressed in a similar fashion and drives expression of GFPuv, resulting in emission of green fluorescence, when the cells are irradiated with UV light. The desired colonies are those that grow in high concentrations of Cm (~100 µg/mL) and NH$_2$Y/DTT and emit green fluorescence upon irradiation, but die at low Cm concentrations (~20 µg/mL) in the absence of NH$_2$Y. Of the 48 colonies tested, 2 met these criteria and were pursued further.

DNA sequencing of the plasmids from these colonies revealed identical RSs with the following residues at the randomized positions: Gln32, Glu65, Gly108, Leu109, Ser158 and Tyr162. Interestingly, residue 32, a Tyr in wt *M. jannaschii* TyrRS and positioned within 2 Å of the C-atom ortho to the hydroxyl group of bound Tyr ligand, is a Gln in the selected RS.[71,72] The crystal structure of wt *M. jannaschii* TyrRS suggests that the Gln allows accommodation of the o-NH$_2$ group and perhaps provides favorable hydrogen bonding interactions. The RS identified from these clones was used for all subsequent experiments.

Figure 2:
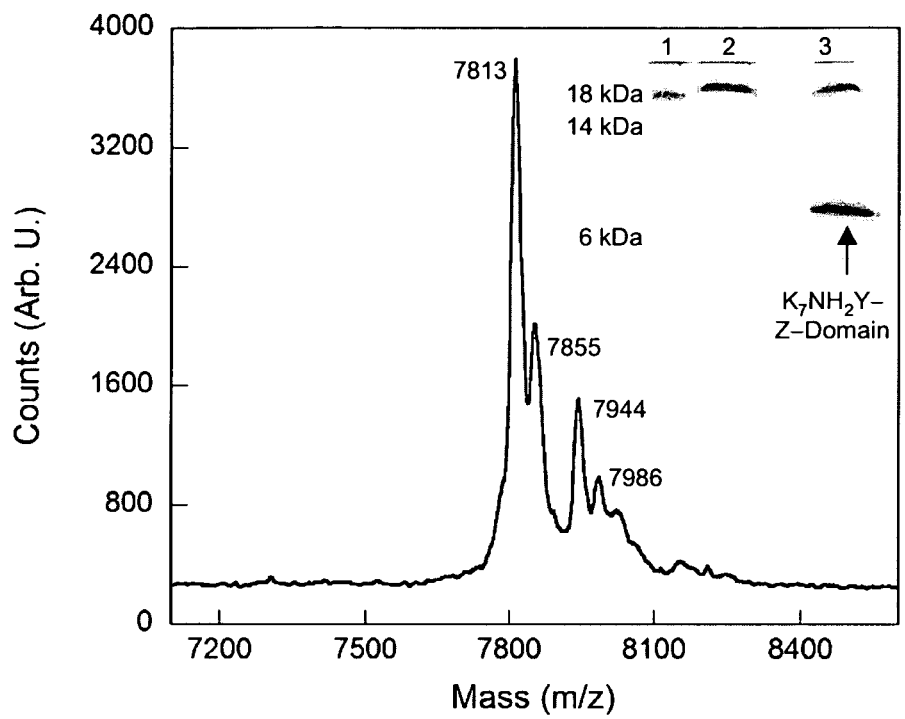
FIG. 2 includes MALDI-TOF MS and SDS PAGE analysis of a $K_7NH_2Y$—Z-domain.

Expression of K$_7$NH$_2$Y—Z-domain. To test the efficiency and fidelity of NH$_2$Y incorporation with the selected RS, the C-terminally His-tagged Z-domain protein (Z-domain), with an amber stop codon at the permissive Lys7 residue, served as a model.[57,73] Expression in the presence of NH$_2$Y/DTT in GMML medium, yielded 5 mg of Z-domain per L culture after purification. SDS PAGE analysis (FIG. 2, inset) demonstrated that in the absence of NH$_2$Y, the amount of Z-domain protein expressed was below the level of detection. The purified protein was subjected to MALDI-TOF MS analysis. Previous studies have shown that the Z-domain is post-translationally modified by removal of the N-terminal Met followed by acetylation of the resulting N-terminal amino acid.[57] Accordingly, MALDI-TOF MS analysis of Z-domain expressed in the presence of NH$_2$Y/DTT revealed four peaks with MW=7812, 7854, 7943 and 7985 Da (FIG. 2). These features correspond to K$_7$NH$_2$Y—Z-domain minus the first Met (MW$_{exp}$=7813 Da), its acetylated form (MW$_{exp}$=7855 Da), full length K$_7$NH$_2$Y—Z-domain (MW$_{exp}$=7944 Da) and its acetylated form (MW$_{exp}$=7986 Da), respectively. Importantly, no K$_7$Y—Z-domain was detected (MW$_{exp}$=7929 Da for the full length form). Together, the studies with the Z-domain demonstrate that the evolved RS is specific for $NH_2Y$ and is efficient at its incorporation into this target protein.

Expression and purification of $NH_2Y$-α2. Having evolved an $NH_2Y$-specific RS and confirmed the efficiency and fidelity of $NH_2Y$ insertion, we next sought an overexpression system for α2 that is compatible with the plasmid/host requirements for $NH_2Y$ incorporation. Several different growth conditions and expression systems were investigated in an effort to maximize α2 production and $NH_2Y$ insertion at residue 730. Growth under anaerobic conditions or in the presence of hydroxyurea was investigated to minimize the reaction of wt β2 with $NH_2Y$-α2, which could lead to premature trapping of an $NH_2Y$. and destruction of the probe. In the former case, the anaerobic class III RNR is operative in *E. coli* and therefore wt class I β2 is not expressed.[1,74] In the latter case, presence of hydroxyurea leads to reduction of the essential $Y_{122}$. in class I β2 so that it cannot react with $NH_2Y$-α2.[75,76] Temperature manipulation was also investigated to minimize inclusion bodies.

Three different expression systems were investigated (see below for details): (1) pBK-$NH_2Y$-RS/pBAD-nrdA, (2) pBK-$NH_2Y$-RS/pMJ1-nrdA and (3) pAC-$NH_2Y$-RS/pMJ1-nrdA (see Table 1). With system (1), expression of full-length α2 at levels 1.5-fold above endogenous α2 were observed. With system (2), only truncated α2 was observed and with system (3) overproduction of truncated α2 was accompanied by expression of full-length α2 that was similar to endogenous levels of α2. The failed or low levels of expression may be due to limiting mut$RNA_{CUA}$ inside the cell and/or the low levels of expression of α2 from the pBAD-nrdA and the pMJ1-nrdA.

The recent report of successful expression and incorporation of unnatural amino acids into *E. coli* nitroreductase using pTrc,[77] prompted us to investigate the pAC-$NH_2Y$-RS/pTrc-nrdA expression system. The pTrc-nrdA vector carries the α2 gene under control of the trp/lac (trc) promoter with the amber stop codon at the desired residue.[78] Importantly, pAC-$NH_2Y$ carries six copies of mut$RNA_{CUA}$ increasing the concentration of the cognate tRNA inside the cell.[63]

Expression of wt α2 from pTrc-nrdA was examined first. Overproduction and subsequent purification, gave 10 mg of pure α2 per g of wet cell paste. This expression level is 2-4× greater than the expression of α2 from pMJ1, which has been routinely used in our lab to express α2 and α2 mutants. In addition, the specific activity of α2 was similar to that produced from pMJ1-nrdA (2500 nmol/min·mg).

Figure 3:
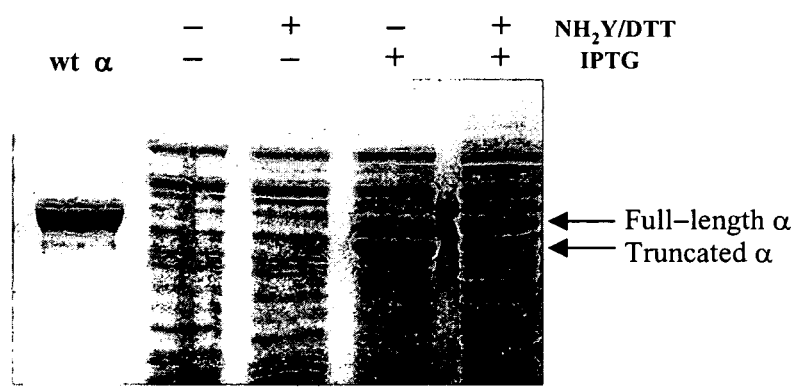
FIG. 3 shows expression of $Y_{731}NH_2Y$-α2. Cells were grown in the presence or absence of IPTG and $NH_2Y$/DTT as indicated and the level of expression assessed by SDS PAGE.
Figure 13:
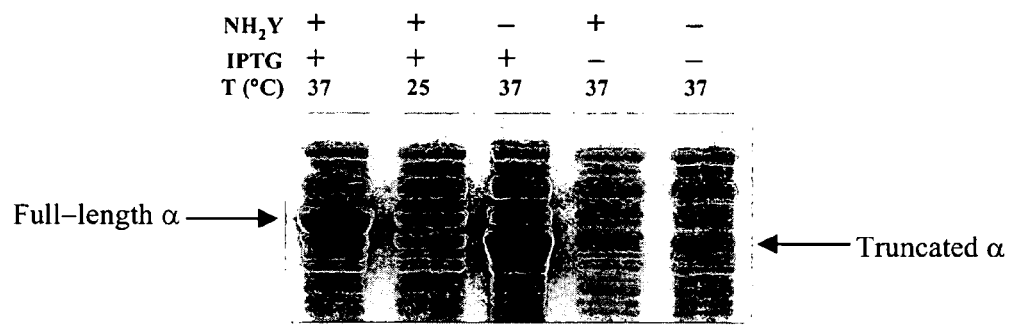
FIG. 13 Expression of $Y_{730}NH_2Y$-α2. Cells were grown in the presence or absence of IPTG and $NH_2Y$/DTT and at 25° or 37° C., as indicated, and the level of expression assessed by SDS PAGE. The position of protein bands for full-length α and truncated cc are denoted by arrows.
Figure 14:
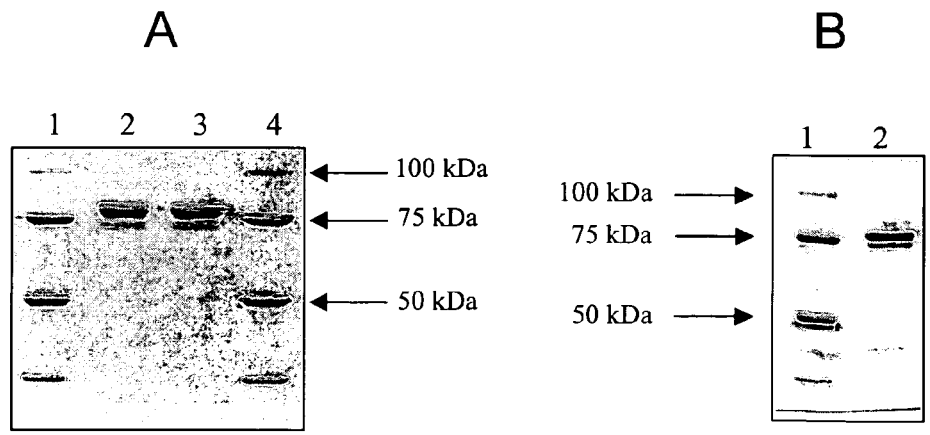
FIG. 14 shows SDS PAGE analysis of purified $Y_{730}NH_2Y$-α2 (A) and $Y_{731}NH_2Y$-β2 (B).

Expression of $Y_{731}NH_2Y$-α2 in DH10B cells doubly transformed with pAC-$NH_2Y$-RS and pTrc-nrdA is shown in FIG. 3. In the presence of the IPTG inducer and $NH_2Y$/DTT, the amber stop codon is suppressed and $NH_2Y$-α2 is overexpressed. In the absence of $NH_2Y$, overproduction of only truncated α2 is observed. Finally, in the absence of inducer IPTG and $NH_2Y$, no overexpression of α2 occurs. A similar profile was obtained for the expression of $Y_{730}NH_2Y$-α2 (FIG. 13). Purification of $NH_2Y$-α2 using dATP affinity chromatography gives 4-6 mg of the target protein per L culture in >90% homogeneity.[55,62] The mutant proteins behaved similarly to wt α2 during the purification procedure (FIG. 14).

Reaction of $NH_2Y$-α2s with wt β2, CDP and ATP monitored by EPR Spectroscopy. The availability of $NH_2Y$-α2s has allowed us to assess the participation of $Y_{730}$ and $Y_{731}$ in a radical propagation across the β2-α2 interface. The experimental design is based on the radical trapping method previously established with DOPA-β2.[38,39] In this method, a stable radical is trapped with an unnatural Y analog that is more easily oxidized than Y. If the trapping requires the presence of β2, substrate, and allosteric effector, then it provides direct evidence for redox activity of that residue during radical propagation. Lack of radical formation may indicate that the residue is not redox-active or that the oxidized product is unstable. We proposed that the ease of oxidation of $NH_2Y$ ($E°$ is 190 mV lower than Y at pH 7) would lead to generation of an $NH_2Y$. allowing its detection by UV-vis and EPR methods.[51] Spectroscopic characterization of $NH_2Y$. has not been previously reported.

Figure 4:
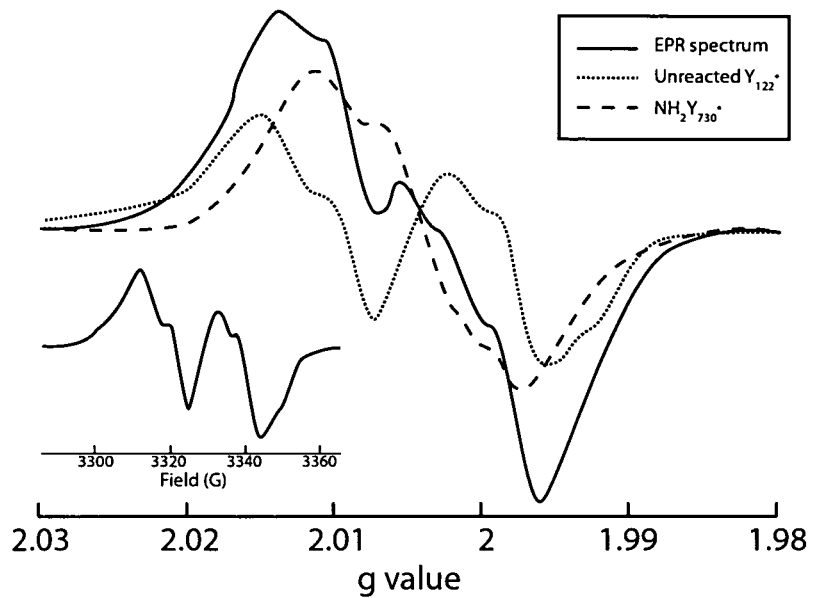
FIG. 4 provides a spectral trace showing reaction of $Y_{730}NH_2Y$-α2/ATP with wt β2/CDP monitored by EPR spectroscopy.

Based on our studies DOPA-β2,[38] we anticipated that the $NH_2Y$. might be stabilized to some extent by the protein environment. With DOPA-β2, maximal amounts of DOPA. were generated by 5 s, which was stable for 2.5 min.[38,39] Thus, $Y_{730}NH_2Y$-α2 (or $Y_{731}NH_2Y$-α2) was mixed with wt β2, substrate (CDP) and effector (ATP), incubated at 25° C. for variable periods of time (10 s to 12 min) and quenched manually in liquid $N_2$. EPR spectra of these reactions revealed a new signal that was present in maximal amounts at the 10 s time point (FIG. 4). A control in the absence of CDP and ATP, revealed only $Y_{122}$. (FIG. 4, inset). Thus formation of the new signal is controlled by the presence of substrate and effector as previously observed with similar studies on DOPA-β2.[38]

The observed spectrum is a composite of at least two species: unreacted $Y_{122}$. and the putative $NH_2Y_{730}$. To reveal the features of the new radical(s), the spectrum of the $Y_{122}$.[14] with distinct, well characterized low field features, was subtracted from the composite signal. The resulting nearly isotropic signal (FIG. 4, dashed line) has an apparent $g_{av}$ of 2.0043 and a peak-to-trough width of 24 G.[79] We ascribe this new signal to $NH_2Y_{730}$.

Figure 5:
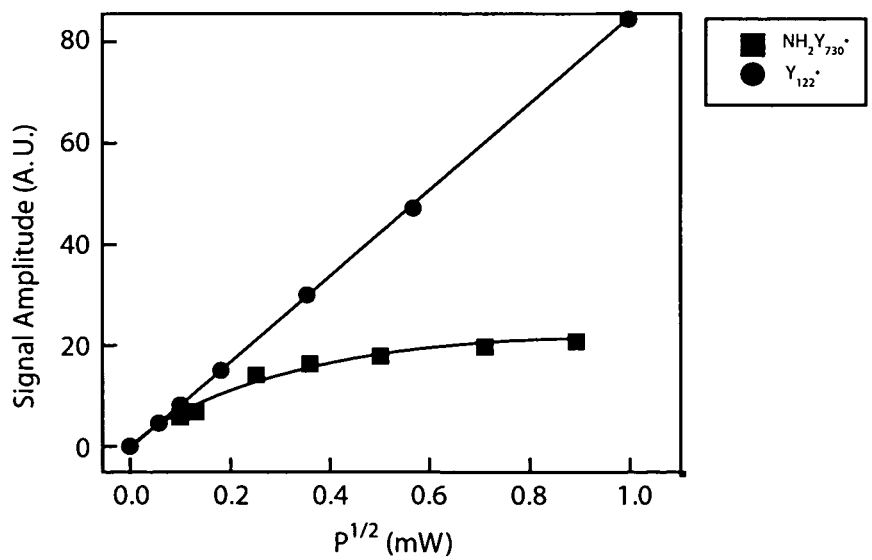
FIG. 5 provides a graph showing microwave power dependence of $Y_{122}$. and $NH_2Y_{730}$. signal intensities.

Spin quantitation at the 10 s time point revealed that 8% of total initial spin (relative to starting $Y_{122}$.) had been lost. Of the remaining spin, 47% is associated with $Y_{122}$. and 53% with the new signal. To further characterize this signal, power saturation studies were carried out. The $Y_{122}$. is adjacent to the diferric cluster, which dramatically alters its relaxation properties. If the new radical is in fact located within α2, >35 Å removed from the diferric cluster as indicated by the docking model, then its $P_{1/2}$ would be markedly reduced. The results of power dependence experiments are shown in FIG. 5. The data were fit to Eq. 1,[80] where K is a sample and instrument dependent scaling factor, P is the microwave power, b is indicative of homogeneous (b=3) or inhomogeneous (b=1) spectral broadening and $P_{1/2}$ is the microwave power at half saturation of the EPR signal.[79,81] For the $Y_{122}$., a $P_{1/2}$ of 28±4 mW was determined, similar to previous measurements.[81,82] The saturation profile of the new signal gave a $P_{1/2}$ of 0.42±0.08 consistent with a radical distant from the diiron center.

$$\text{Signal Amplitude} = \frac{K \times (\sqrt{P})}{[1 + (P/P_{1/2})]^{0.5 \times b}} \quad (1)$$

Figure 6:
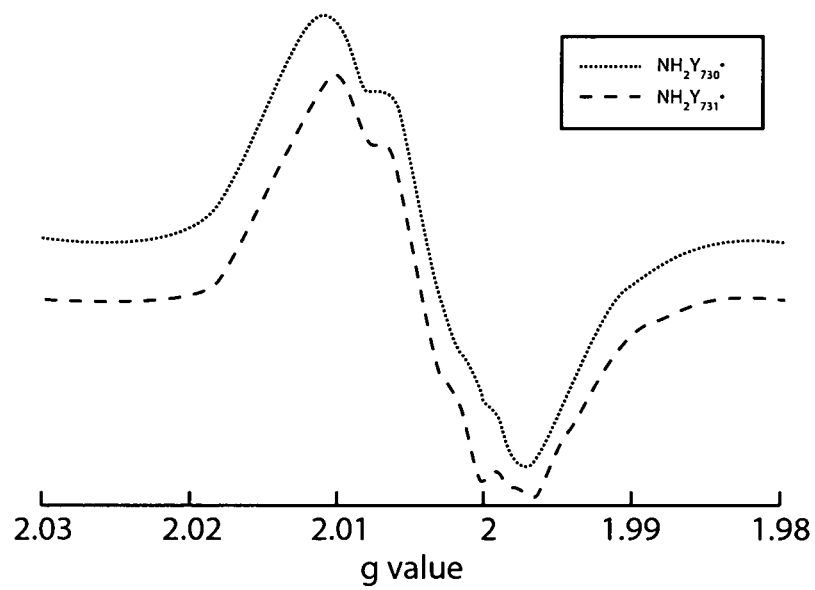
FIG. 6 Comparison of the $NH_2Y_{730}$. (dotted line, FIG. 4) and $NH_2Y_{731}$. (dashed line, FIG. 15).
Figure 15:
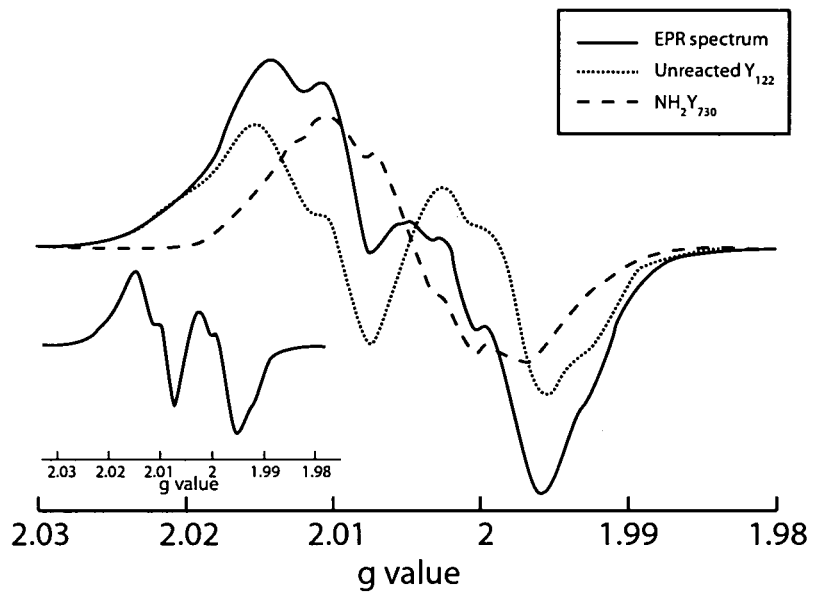
FIG. 15 depicts the results of a reaction of $Y_{731}NH_2Y$-α2/ATP with wt β2/CDP monitored by EPR.

Similar experiments have also been carried out with $Y_{731}NH_2Y$-α2. A new signal, the putative $NH_2Y_{731}$., is also observed only in the presence of CDP/ATP (FIG. 15). Subtraction of the $Y_{122}$. spectrum, reveals a spectrum that is similar, but not identical, to that of $NH_2Y_{730}$. (FIG. 6). The nearly isotropic signal associated with $NH_2Y_{731}$. consists of a $g_{av}$ of 2.0044 and a peak-to-trough width of 22 G. At the 10 s time point, 14% of total initial spin has been lost. Of the remaining spin, 45% is associated with $NH_2Y_{731}$. and 55% with $Y_{122}$.

Kinetics of $NH_2Y$.—α2 formation monitored by SF UV-vis spectroscopy. Pre-steady state experiments were carried out to assess whether $NH_2Y$.-α2 formation occurs with a rate constant fast enough to be competent in nucleotide reduction in wt RNR. Previous steady state and pre-steady state kinetic analysis of E. coli RNR monitoring nucleotide reduction have shown that radical propagation is preceded by a slow conformation change.[83] This slow physical step masks intermediates that form in the propagation process. In the presence of CDP/ATP, and at concentrations of α2 and β2 used in the present study, the rate constant for this conformational change varies from ~4-17 $s^{-1}$.[83] The steady state rate constant for dCDP formation is on the order of 2 $s^{-1}$ and is thought to be limited by re-reduction of the active site disulfide that accompanies dCDP formation, or by a conformational change associated with re-reduction. In previous studies with DOPA-β2, α2 and CDP/ATP, DOPA. formation occurred in two fast kinetic phases (38.0 and 6.8 $s^{-1}$) and a slow phase (0.7 $s^{-1}$). Thus, the two fast phases in the DOPA-β2 experiments, and potentially the third phase,[84] were kinetically competent with respect to the conformational change, which limits dCDP formation in the first turnover.[83]

Figure 7:
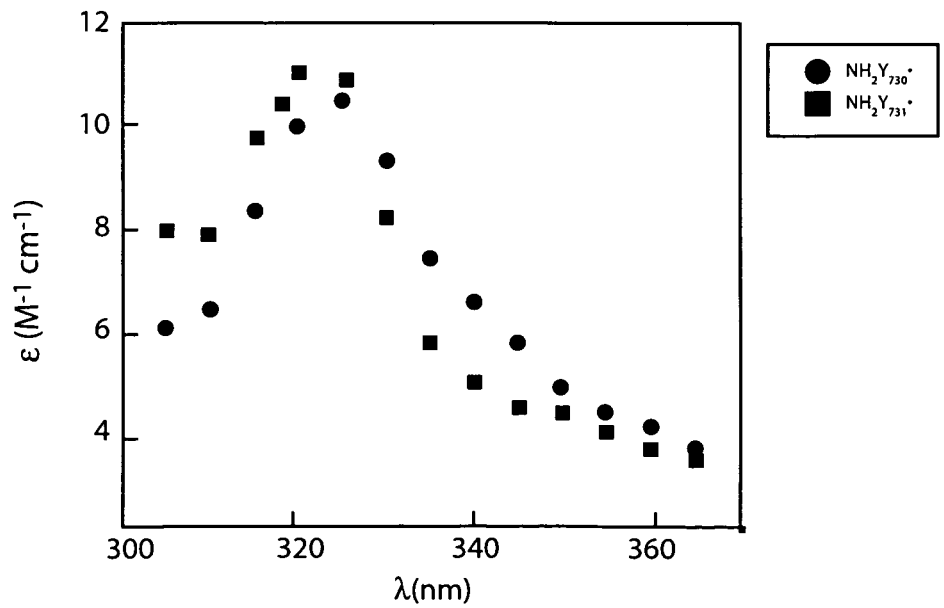
FIG. 7 Point-by-point reconstruction of the UV-vis spectrum of $NH_2Y_{730}$. (circles) and $NH_2Y_{731}$. (squares).

To monitor changes in the concentration of $NH_2Y.$, its spectrum and extinction coefficient must be determined. Our initial assumption was that its UV-vis spectrum would be similar to that of DOPA. ($\lambda_{max}$ at 315 nm and $\in$~12000 $M^{-1}cm^{-1}$).[38,85] The extinction coefficients associated with $Y_{122}.$ between 310 and 365 nm are low ($\in$~500-1900 $M^{-1}cm^{-1}$) and can be used in spectral deconvolution.[66,67] Thus, using SF spectroscopy, we carried out a point-by-point analysis of the UV-vis properties of the new radical. $Y_{730}NH_2Y$-α2 (or $Y_{731}NH_2Y$-α2) and ATP in one syringe was mixed with wt β2 and CDP from a second syringe and the absorbance monitored from 305-365 nm in 5 nm intervals. The absorbance change at 1.5 s at each λ, corrected for the absorption by the $Y_{122}.$,[66,67] was then plotted against the λ. The results are shown in FIG. 7 and indicate that $NH_2Y_{730}.$ and $NH_2Y_{731}.$ have similar, but distinct absorption profiles. The UV-vis spectrum of $NH_2Y_{730}.$ consists of a broad feature with a $\lambda_{max}$ at 325 nm ($\in$~10500 $M^{-1}$ $cm^{-1}$). The $NH_2Y_{731}.$ spectrum exhibits a $\lambda_{max}$ at 320 nm ($\in$~11000 $M^{-1}$ $cm^{-1}$) and a more defined shoulder at 350 nm. The extinction coefficients for $NH_2Y.$-α2s were determined using $\in$ for $Y_{122}.$ at 410 $nm^{68}$ and the assumption that loss of each mole of $Y_{122}.$ leads to formation of one mole of $NH_2Y$.

Figure 8:
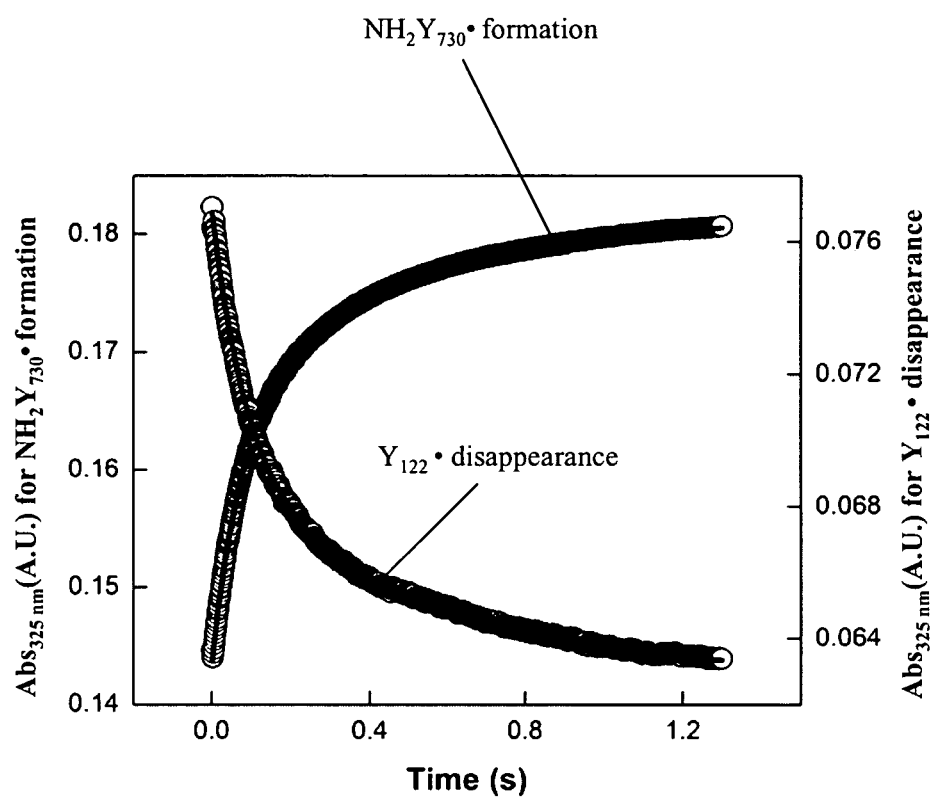
FIG. 8 is a graph showing stopped flow kinetics of $NH_2Y_{730}$. formation.

SF UV-vis experiments carried out to monitor the kinetics of loss of $Y_{122}.$ (410 nm) and formation of $NH_2Y$. (325 nm) are shown in FIG. 8 for $Y_{730}NH_2Y$-α2. At 410 nm, bi-exponential kinetics with rate constants of 12.0±0.1 $s^{-1}$ and 2.4±0.1 $s^{-1}$ were observed, similar to rate constants obtained for formation of $NH_2Y$. at 325 nm (13.6±0.1 $s^{-1}$ and 2.5±0.1 $s^{-1}$). Analogous experiments carried out with $Y_{731}NH_2Y$-α2 showed that loss of $Y_{122}.$ occurred bi-exponentially (17.3±0.2 and 2.3±0.1 $s^{-1}$) concomitant with formation of $NH_2Y_{731}.$ (21.0±0.1 $s^{-1}$ and 3±0.1 $s^{-1}$, FIG. 16). The rate constants and amplitudes for both reactions are summarized in Table 2. A control experiment was carried out in the absence of substrate and effector with $Y_{730}NH_2Y$-α2 (or $Y_{731}NH_2Y$-α2) and 132. As indicated by EPR experiments, no loss of $Y_{122}.$ or formation of $NH_2Y$. occurred under identical conditions.

As noted above, the fast rate constants observed with the $NH_2Y$-α2s are kinetically competent in RNR turnover. Thus studies with these mutants provide the first direct evidence for their involvement in radical propagation. The slow rate constant, also observed in the DOPA-β2 experiments, is similar to the steady state rate constant for RNR turnover. A possible explanation for this slow phase is discussed below.

Finally, analysis of the amounts of each radical at 2 s shows that with $Y_{730}NH_2Y$-α2 and $Y_{731}NH_2Y$-α2, 39% and 35% of total initial $Y_{122}.$ is consumed, respectively. In contrast with the DOPA-β2, the $NH_2Y$. is less stable. The instability needs to be assessed in detail and requires kinetic analysis using rapid freeze quench methods to unravel its mechanistic implications.

Activities of $NH_2Y$-α2s. Recently, using a series of $F_nY_{356}$-β2s, we found a correlation between nucleotide reduction activity and the reduction potential of residue 356, when its potential was 80 to 200 mV higher than that of tyrosine.[40,43] The reduction potential of DOPA is 260 mV lower than that of Y (pH 7) and with DOPA-β2,[38] deoxynucleotide formation was below our lower limit of detection. With $NH_2Y$-α2, the potential of $NH_2Y$ is 190 mV lower than that of Y (pH 7).[51] To test whether this energy barrier would be large enough to shut down radical transfer to $C_{439}$, and therefore nucleotide reduction, activity assays were performed on $NH_2Y$-α2s.

Activity was determined by monitoring dCDP formation indirectly (spectrophotometric assay) or directly (radioactive assay). The activities determined using these assays are summarized in Table 3. The results show nucleotide reduction activity for $Y_{730}NH_2Y$-α2 and $Y_{731}NH_2Y$-α2 that is 4% and 7% that of wt α2, respectively. The observed activity may be inherent to $NH_2Y$-α2s; on the other hand, it may be ascribed to co-purifying endogenous wt α2 or to wt α2 generated by the host cell as a result of amber codon suppression with Tyr-loaded $mutRNA_{CUA}$ in place of $NH_2Y$-loaded $tRNA_{CUA}$.

To distinguish between these two options, assays with $N_3ADP$ were carried out. $N_3ADP$ is a mechanism-based inhibitor of class I RNRs which generates a moderately stable N-centered nucleotide radical (N.) covalently bound to the nucleotide and a cysteine in the active site of α2.[28-31,86] This radical may be used as a reporter of the ability of $NH_2Y$. to generate a $C_{439}$. and initiate chemistry on the nucleotide. Previous studies of the inactivation of wt α2β2 by $N_3ADP$/dGTP suggest that on a 20 s time scale, 50-60% of the initial $Y_{122}.$ is lost leading to formation of an equivalent amount of N.[30,62] Therefore, if the activity observed with $NH_2Y$-α2s is indicative of wt α2, ~2% and ~3.5% of total initial $Y_{122}.$ would be expected to form a N. with $Y_{730}NH_2Y$-α2 and $Y_{731}NH_2Y$-α2, respectively.

Figure 9A:
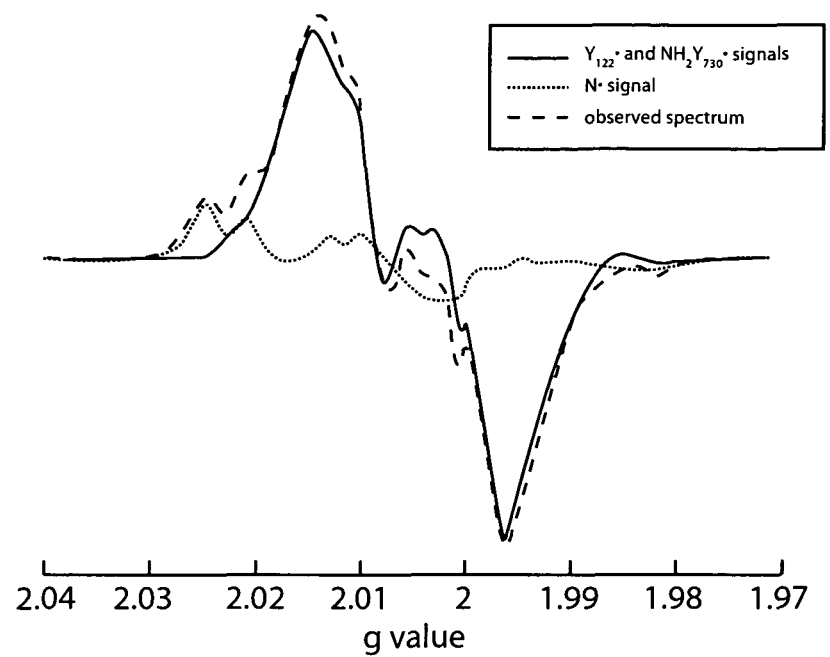
FIG. 9 provides dual spectrums showing formation of N. from $N_3$ADP upon incubation with $Y_{730}NH_2Y$-α2, β2 and dGTP.
Figure 9B:
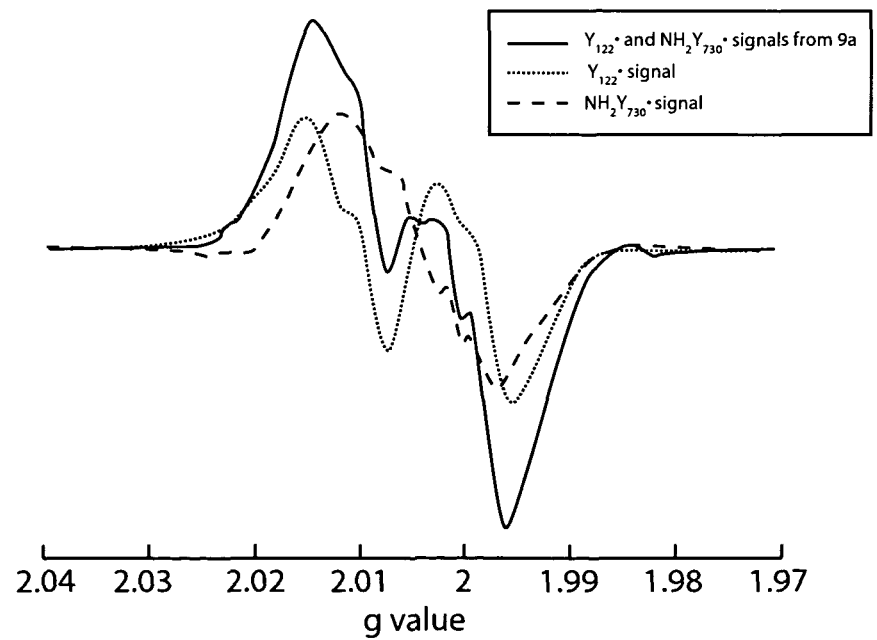
Figure 10:
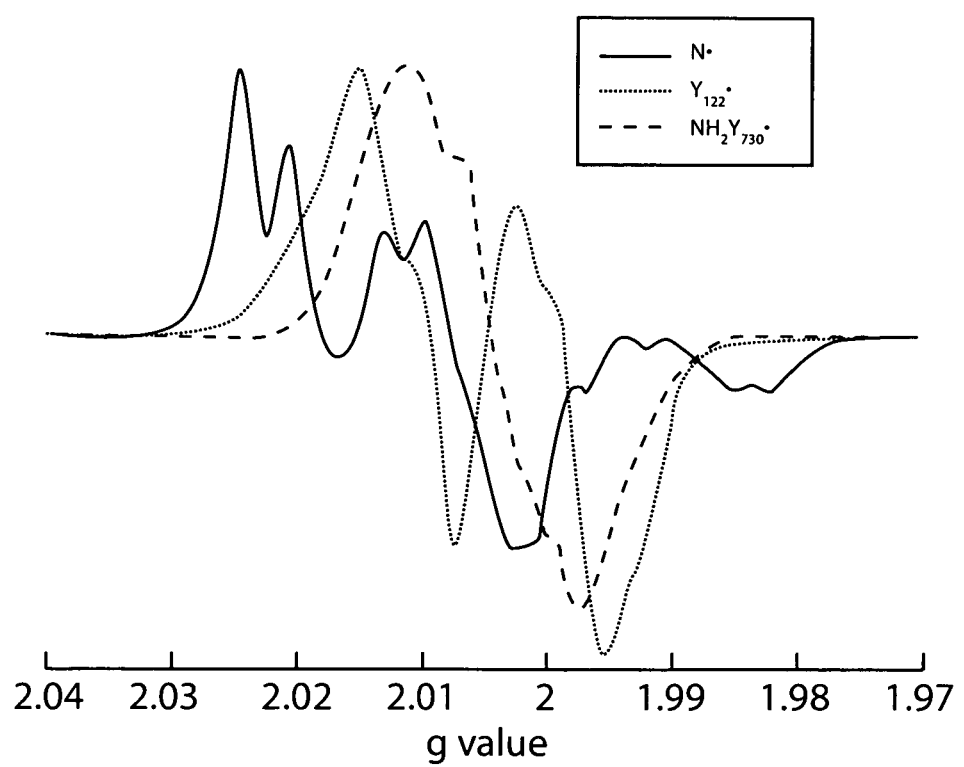
FIG. 10 Spectral comparison of N. (black), $Y_{122}$. (dotted line), and $NH_2Y_{730}$. (dashed line).

Assays with $N_3ADP$ were carried out by mixing each $NH_2Y$-α2 (or wt α2) and dGTP with wt 132 and $N_3ADP$. After 20 s the reaction was hand-quenched in liquid $N_2$. The EPR spectrum obtained for $Y_{730}NH_2Y$-α2 is shown in FIG. 9. The observed spectrum is a combination of at least three radicals: $Y_{122}.$, $NH_2Y_{730}.$, and N. The spectrum can be deconvoluted using the differences in spectral widths and unique spectral features within these regions (FIG. 10). Thus, the data were analyzed by first subtracting the N. spectrum, which contains the broadest of the three signals. The resulting spectrum was then subjected to fractional subtraction of the $Y_{122}.$ component, yielding the $NH_2Y_{730}.$ signal. The concentration of each of the radicals was determined using standard EPR quantitation methods.[65]

The results from this quantitative analysis are shown in Table 4. They show that 18% of the total spin has been lost at the 20 s time point. Of the remaining spin, 19±2% is associated with N.; 43% is $Y_{122}.$ and 39% is $NH_2Y_{730}.$ Accounting for the lost spin after 20 s, 15±2% of total initial $Y_{122}.$ (i.e. at t=0) leads to N. formation. With $Y_{731}NH_2Y$-α2 (FIG. 17 & Table 4), 25% of the total spin is lost after 20 s with 20±2% present as N., 41% as $Y_{122}.$ and 39% as $NH_2Y_{731}.$. Accounting for the lost spin after 20 s, 15±2% of total initial $Y_{122}.$ leads to formation of N. Therefore, with both mutants, the amount of N. observed exceeds the 2% or 3.5% N. (for $Y_{730}NH_2Y$-α2 and $Y_{731}NH_2Y$-α2, respectively), expected if the steady state activity was due to contaminating wt α2. These results strongly suggest that $NH_2Y$-α2s are competent in $C_{439}$. formation and thus nucleotide reduction.

TABLE 1

Vectors used in this study.

| Plasmid | Description | Reference |
|---|---|---|
| pBK-JYRS | M. jannaschii TyrRS library, $Kan^R$ | 46 |
| pREP/YC-J17 | Positive selection plasmid: CAT ($Asp_{112}TAG$), T7 RNAP ($Met_1TAG$, $Gln_{107}TAG$), $mutRNA_{CUA}$, GFPuv, $Tet^R$ | 56 |
| pLWJ17B3 | Negative selection plasmid: barnase ($Gln_2TAG$, $Asp_{44}TAG$, $Gly_{65}TAG$), $mutRNA_{CUA}$, $Amp^R$ | 57, 58 |
| pBK-$NH_2$Y-RS | $NH_2$Y-RS, $Kan^R$ | This study |
| pLEIZ | Z-Domain, $Cm^R$ | 57, 59 |
| pTrc-nrdA | nrdA expression vector: nrdA ($Tyr_{730}TAG$ or $Tyr_{731}TAG$) with trc promoter, $Amp^R$ | This study |
| pAC-$NH_2$Y-RS | $NH_2$Y-RS, 6 × $mutRNA_{CUA}$, $Tet^R$ | This study |
| pMJ1-nrdA | nrdA expression vector: nrdA with T7 promoter, $Amp^R$ | This study |
| pBAD-nrdA | nrdA expression vector: nrdA with L-Ara promoter, $mutRNA_{CUA}$, $Tet^R$ | This study |

TABLE 2

Summary of Kinetic Data for Formation of $NH_2Y\bullet$-$\alpha 2$.

| RNR Subunits | CDP/ATP | $1^{st}$ Phase $k_{obs}$ ($s^{-1}$)[a], Ampl[b] (%) | $2^{nd}$ Phase $k_{obs}$ ($s^{-1}$)[a], Ampl[b] (%) |
|---|---|---|---|
| $Y_{730}NH_2Y$-$\alpha 2\beta 2$ | NO | [c] | [c] |
| $Y_{730}NH_2Y$-$\alpha 2\beta 2$ | YES | 12.8 ± 0.8, 20 ± 1 | 2.5 ± 0.1, 19 ± 1 |
| $Y_{731}NH_2Y$-$\alpha 2\beta 2$ | NO | [c] | [c] |
| $Y_{731}NH_2Y$-$\alpha 2\beta 2$ | YES | 19.2 ± 1.8, 24 ± 1 | 2.7 ± 0.4, 11 ± 1 |

[a] The rate constants reported are the average of those measured at 410 nm (for $Y_{122}\bullet$ loss) and at 320 nm (for $NH_2Y_{731}\bullet$ formation) or 325 nm (for $NH_2Y_{730}\bullet$ formation). The error corresponds to the standard deviation between these two measurements.
[b] Ampl, amplitude; the amount of $Y_{122}\bullet$ trapped in each kinetic phase is indicated as a % of total initial $Y_{122}\bullet$. Because the determination of ε for $NH_2Y\bullet$ was based on that of $Y_{122}\bullet$, the amplitudes at 410 nm and 320 or 325 nm are nearly identical.
[c] No changes observed.

TABLE 3

Monitoring the Activity of $NH_2Y$-$\alpha 2$s by measuring deoxynucleotide and N• formation.

| α2 Variant | Spectrophotometric RNR Assay (% wt)[a] | Radioactive RNR Assay (% wt)[a] | $N_3$ADP Assay (% N• at 20 s,[b] % N• vs. initial $Y_{122}\bullet$[c]) |
|---|---|---|---|
| wt α2 | 100[a] | 100[a] | 52 |
| $Y_{730}NH_2Y$-α2 | 4 ± 0.3 | 4 ± 0.5 | 19 ± 2,[b] 15 ± 2[c] |
| $Y_{731}NH_2Y$-α2 | 7 ± 1 | 7 ± 0.5 | 20 ± 2,[b] 15 ± 2[c] |

[a] The activity is reported as % of wt activity, which was 2500 nmol/min · mg. The error is the standard deviation from 3 independent measurements for the spectrophotometric assay and 2 independent measurements for the radioactive assay.
[b] The amount of N• is indicated as % of total spin at 20 s; the error is associated with EPR spin quantitation methods.
[c] The amount of N• is indicated as % of the total initial $Y_{122}\bullet$; the error is associated with EPR spin quantitation.

TABLE 4

Analysis of the reaction of wt α2 or $NH_2Y$-α2s with β2 and $N_3$ADP/dGTP at 20 s.[a]

| α2 Variant | $[Spin]_T$ (μM)[b] | [N•] (μM) | $[Y_{122}\bullet]$ (μM) | $[NH_2Y\bullet]$ (μM) |
|---|---|---|---|---|
| wt α2 | 22.9 | 11.9 | 11.0 | — |
| $Y_{730}NH_2Y$-α2 | 19.5 | 3.7 | 8.4 | 7.6 |
| $Y_{731}NH_2Y$-α2 | 18.1 | 3.6 | 7.5 | 7.1 |

[a] The error associated with EPR quantitation was ~10%.
[b] In each case, the initial $[Y_{122}\bullet]$ was 24 μM.

Cloning of pBAD-nrdA and Insertion of TAG codons. Vector pBAD-JYCUA was obtained from the Schultz lab (ref. 61, text). The nrdA gene was cloned from pMJ1-nrdA into pBAD-JYCUA using the NcoI and KpnI restriction sites by standard methods to yield pBAD-nrdA. Insertion of TAG codons at positions 730 and 731 was carried out as described for pTrc-nrdA using primers 3-6 (see Methods). The mutations were confirmed by sequencing the entire gene at the MIT Biopolymers Laboratory.

Generation of pMJ1-nrdA730TAG and pMJ1-nrdA731TAG. Vector pMJ1-nrdA has been reported before (ref. 60, text). Insertion of TAG codons at positions 730 and 731 was carried out as described for pTrc-nrdA using primers 3-6 (see Methods). The mutations were confirmed by sequencing the entire gene at the MIT Biopolymers Laboratory.

Attempts at Expression of $Y_{730}NH_2Y$-α2. In an effort to maximize production of α2 containing $NH_2Y$, without generation of $NH_2Y$., growth conditions were examined at different temperatures, under aerobic and anaerobic conditions and with hydroxyurea in the media to reduce the $Y_{122}$. in wt 132.

In each case, a single colony of DH10B or BL21(DE3) E. coli cells was used to inoculate a 5 mL 2YT small culture. After saturation, this culture was diluted 100-fold into 2×100 mL GMML media. When $OD_{600\,nm}$ was ~0.6-0.8, and after the variations detailed below, one flask was supplemented with $NH_2Y$ and DTT to final concentrations of 1 mM and 0.1 mM, respectively. The other growth served as the control. After 15 min, expression of $NH_2Y$-α2 was induced by addition of IPTG to both 100 mL cultures (or 0.2% (w/v) L-arabinose with expression system (1)—see below). Small aliquots were removed from each flask after a defined time period (5-12 h) and expression of α2 assessed by SDS PAGE analysis in the presence and absence of $NH_2Y$/DTT.

When the effect of temperature on expression of $Y_{730}NH_2Y$-α2 was tested, growth conditions for the small culture were identical to those above. When $OD_{600\,nm}$ was ~0.6-0.8, the temperature setting was changed to 25 or 30° C. After 15 min, $NH_2Y$ and DTT were added and the growth was continued as described above.

When the effect of $Y_{122}$.-β2 on expression of $Y_{730}NH_2Y$-α2 was tested, growth conditions for the small culture were identical to those described above. When $OD_{600\,nm}$ was 0.6-0.8, hydroxyurea was added to a final concentration of 65 mM. After 15 min, $NH_2Y$ and DTT were added to final concentrations of 1 mM and 0.1 mM, respectively. After an additional 15 min, induction was carried out as above. Each hour after induction, the culture was supplemented with an additional 15 mM hydroxyurea.

When the effect of $O_2$ on expression of $Y_{730}NH_2Y$-α2 was tested, growth conditions for the small culture were identical to those described above. When the small culture was saturated, it was diluted 100-fold into a 250 mL 2YT medium containing the appropriate antibiotics in a 1 L Erlenmeyer flask. At saturation, the culture was diluted 50-fold into 5-7 L GMML medium in a fermentor flask with appropriate antibiotics. When $OD_{600\,nm}$ was 0.6-0.8, the air was replaced with $N_{2(g)}$. After 15 min, $NH_2Y$ and DTT were added to final concentrations of 1 mM and 0.1 mM, respectively, and the growth continued as described above.

Several expression systems were tested: (1) the pBK-$NH_2Y$-RS/pBAD-α2 expression system was investigated, in which pBK-$NH_2Y$-RS carries the $NH_2Y$-RS gene under control of the constitutive E. coli Gln-RS promoter and terminator and a $Kan^R$ marker, and vector pBAD-α2 carries the α2 gene with the appropriate amber codon under control of an L-Ara-inducible promoter and a rrnB terminator as well as the mutRNA$_{CUA}$ gene under control of a lpp promoter and rrnC terminator and a Tet$^R$ marker; (2) The pBK-NH$_2$Y-RS/pMJ1-nrdA vector combination was examined, in which vector pMJ1-nrdA carries the nrdA gene with the amber codon under control of T7 promoter and terminator and a Amp$^R$ marker. (3) The pAC-NH$_2$Y-RS/pMJ1-nrdA system was also examined, where pAC-NH$_2$Y-RS carries the NH$_2$Y-RS gene under control of glnS' promoter and rrnB terminator, six copies of the mutRNA$_{CUA}$ gene under control of a proK promoter and terminator and a Tet$^R$ marker (Table 1).

Discussion

Generation of Y$_{730}$NH$_2$Y-α2 and Y$_{731}$NH$_2$Y-α2. In this study, we have evaluated the proposed roles for residues Y$_{730}$ and Y$_{731}$ in radical propagation, by site-specifically replacing them with NH$_2$Y (FIG. 1). We employed the in vivo suppressor tRNA/RS method, which has been pioneered[46] and developed[47-50] by the Schultz lab and promises to have an immense impact on protein biochemistry. Using this technology, we evolved the desired tRNA/RS pair, which allowed us to generate Y$_{730}$NH$_2$Y-α2 and Y$_{731}$NH$_2$Y-α2 in yields of 4-6 mg per g of wet cell paste. The large size of α2 (172 kDa) and the small size difference between NH$_2$Y and Y have precluded quantitative assessment of NH$_2$Y incorporation into α2 by direct ESI or MALDI TOF mass spectrometric methods. Analytical methods using LC/MS of tryptic digests of this 172 kDa protein, to evaluate levels of NH$_2$Y relative to Y in NH$_2$Y-α2s, are currently being developed. Nevertheless, our studies with the model Z-domain protein indicate that incorporation of NH$_2$Y is efficient and specific. In addition, evaluation of our NH$_2$Y-α2 preparations, using N$_3$ADP and dCDP assays, also suggest presence of low levels of wt α2.

The ability to incorporate NH$_2$Y site-specifically into proteins will be of general use. Our characterization of the UV-vis and EPR spectroscopic properties of the NH$_2$Y. should allow NH$_2$Y to serve as a probe for enzymes that are thought to employ transient Y.s in catalysis or in electron transfer between metal centers. In addition, Francis and colleagues have recently shown that NH$_2$Y may be derivatized with fluorescent dyes.[87,88] Thus, NH$_2$Y may also be utilized as a tool for site-specifically appending probes of interest to the target protein.

Structural assignment of the new radical. When NH$_2$Y-α2s are reacted with β2, in the presence of CDP/ATP, a new EPR-active signal is observed. As noted above, however, neither UV-vis, nor EPR spectral properties of the NH$_2$Y. had previously been reported. The assignment of our new signal to NH$_2$Y. is based on SF UV-vis and EPR spectroscopic measurements in conjunction with knowledge of the properties of DOPA, catechol, and o-aminophenol radicals.[89,90] First, point-by-point reconstruction of the new radical's UV-vis spectrum by SF methods reveals an absorption spectrum similar to DOPA., which is expected based on the structural similarity between these two amino acids. Second, subtraction of the Y$_{122}$. EPR spectrum from the observed EPR signal, yields a spectrum with a g$_{av}$ of 2.0043±0.0001 which is typical of organic radicals. The small hyperfine couplings (<10 G) from the ring protons and from the amine nitrogen are similar to those previously reported for o-aminophenol radicals.[89] Third, information about the location of the new radical relative to the diferric cluster has been obtained by power saturation studies. These studies show that Y$_{122}$. saturates with a P$_{1/2}$ of 28 mW due to its vicinity to the diferric cluster (4.6 Å to the nearest iron in the cluster).[19] Mechanism based inhibitors that covalently label the active site of α2, >35 Å from the cluster, have P$_{1/2}$ values of 0.16 mW.[82] The new radical has a P$_{1/2}$ of 0.42±0.08 mW consistent with a species distant from the diiron center. These data together strongly suggest that the new radical is NH$_2$Y. (FIG. 1, Scheme 1).[91] High field EPR and ENDOR experiments, isotopic labeling studies with $^{15}$N and $^2$H in conjunction with computational studies are in progress to further support this assignment.

Kinetics of NH$_2$Y.-α2 formation. SF kinetic studies give rate constants of 12.8 and 2.5 s$^{-1}$ for Y$_{730}$NH$_2$Y-α2, and 19.2 and 2.7 s$^{-1}$ for Y$_{731}$NH$_2$Y-α2. The fast rate constant is indicative of a rate-determining conformational change, which has previously been found to precede radical propagation in wt β2, under single turnover conditions.[83] Thus, formation of NH$_2$Y. occurs in a kinetically competent fashion at the expense of the Y$_{122}$.[38] Further, as with DOPA, NH$_2$Y acts as a conformational probe and allows direct detection of this physical step, reporting on the regulatory state of the NH$_2$Y-α2β2 complex. The slow rate constant observed in these kinetic studies has also been observed when monitoring DOPA$_{356}$. formation (0.4 to 0.8 s$^{-1}$ with different substrate/effector pairs).[38, 84] These rate constants are all in the same range, similar to the turnover number of RNR at the protein concentrations used in these experiments. Our previous studies have suggested that in the steady state, re-reduction of the disulfide or a conformational change associated with this process is rate-limiting. If the latter is the case, then this rate constant of 2-3 s$^{-1}$, might be indicative of the slow conversion of one form of RNR into the more active form. Alternatively, incorporation of NH$_2$Y could result in α2 with two conformations of the tyrosine analogue that do not interconvert rapidly or two different conformations of the α2 itself. The separate kinetic phases for NH$_2$Y. formation indicate that these two conformations do not interconvert on the time scale of the SF experiment. Additional kinetic analysis can further assign the nature of the slow rate constant observed.

Activity Assays of NH$_2$Y-α2s. Steady state turnover measurements show the ability of both mutant proteins to produce dNDPs. As noted above, this activity could be associated with endogenous wt α2, which co-purifies with NH$_2$Y-α2s, or with wt α2 which is generated by suppression of the amber codon with Tyr-loaded tRNA$_{CUA}$ in place of NH$_2$Y. Alternatively, the activity may be inherent to NH$_2$Y-α2s.

To distinguish between these options, experiments with the mechanism-based inhibitor N$_3$ADP were carried out. The results indicate 15±2% N. formation with Y$_{730}$NH$_2$Y-α2 and Y$_{731}$NH$_2$Y-α2. These values exceed the expected 2% and 3.5%, respectively, if the steady state turnover were due to background levels of wt α2. Thus, the results suggest that NH$_2$Y-α2s are competent in nucleotide production. This implies that the putative NH$_2$Y. is an intermediate during active radical transport. Detailed kinetic analysis on the ms time scale will further test this proposition. If true, then these observations would mark the first detection of an amino acid radical during long-range hole migration in an RNR variant that is competent in dNDP formation.

Figure 11:
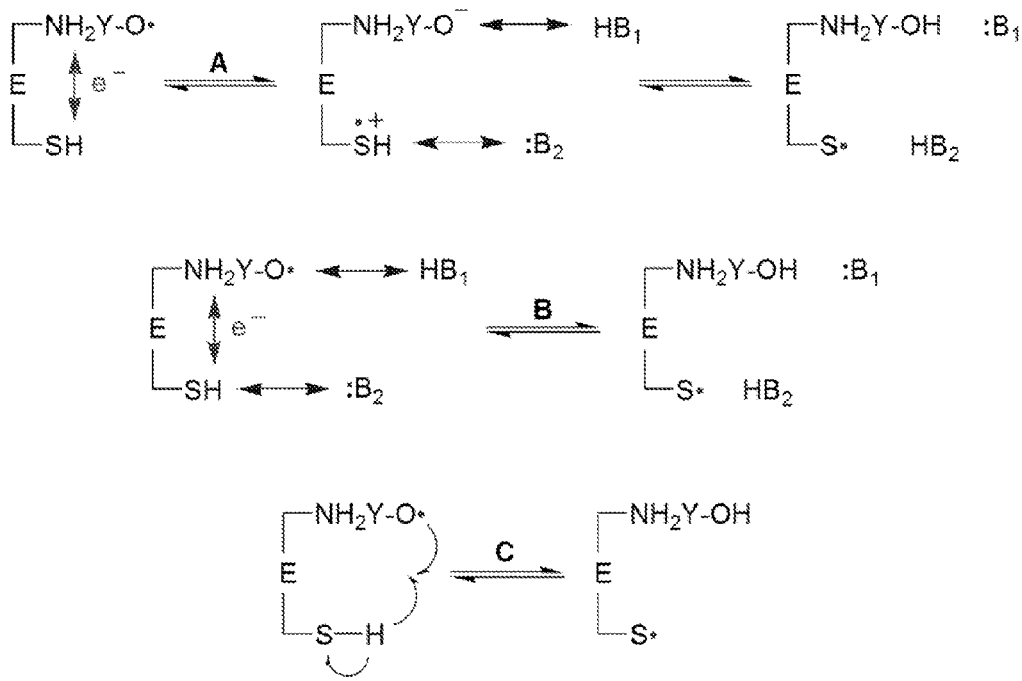
FIG. 11 shows mechanistic options for oxidation of C439 by NH2Y730.

Implications for mechanism of oxidation. Competence in nucleotide reduction has interesting mechanistic implications for radical propagation within Y$_{730}$NH$_2$Y-α2. Three mechanisms may be envisioned for oxidation of C$_{439}$ by NH$_2$Y$_{730}$.: This reaction may occur by (1) a stepwise process, i.e. electron transfer followed by proton transfer, (2) an orthogonal proton-coupled electron transfer (PCET) or (3) a co-linear PCET (i.e. hydrogen atom transfer, FIG. 11).[92-94] The option of the stepwise process may be eliminated due to thermochemical bias against formation of high energy charged intermediates in the non-polar α2 active site as well as the insurmountable energy barrier for formation of a cysteine cation radical by the NH$_2$Y./NH$_2$Y$^-$ couple (FIG. 11A).[93] Orthogonal PCET requires oxidation of C$_{439}$, which has a solution reduction potential of 1.33 V at pH 7, by a $NH_2Y$. which has E° of 0.64 V at pH 7 (FIG. 11B).[1,51] Therefore, the second option would require a thermodynamically uphill process that is unfavorable by 16 kcal/mol. The hydrogen atom transfer mechanism, however, is thermodynamically more accessible (FIG. 11C). Its feasibility is based on knowledge of the homolytic bond dissociation energies of R-SH (88-91 kcal/mol) and o-aminophenol, calculated to be 78-83 kcal/mol.[1,95-97] Therefore, oxidation of $C_{439}$ by $NH_2Y_{730}$. by a hydrogen atom transfer mechanism, assuming no perturbations in the protein milieu, is uphill by 'only' 5-13 kcal/mol. Thus, nucleotide reduction activity in $Y_{730}NH_2Y$-α2 would thermodynamically favor a hydrogen atom transfer mechanism for $C_{439}$. formation by $NH_2Y_{730}$.

Interestingly, the bond dissociation energy of catechol (82-83 kcal/mol) is similar to that of o-aminophenol.[95] However, $DOPA_{356}$-β2 is inactive in nucleotide reduction. In case of DOPA-β2 orthogonal PCET, the functional mechanism of oxidation at this residue (i.e. similar to FIG. 11B), requires matching redox potentials for efficient radical propagation and nucleotide reduction. With, $Y_{730}NH_2Y$-α2, competence in nucleotide reduction, despite unmatched redox potentials (~0.69 V difference), appears to be reconciled due to a different mechanism of oxidation via hydrogen atom transfer, which appears to operate at this residue in the pathway.

In conclusion, we report evolution of a suppressor tRNA/RS pair that is specific for the unnatural amino acid $NH_2Y$. Site-specific insertion of $NH_2Y$ will be useful for other systems that use Y.s in catalysis and for attaching probes of interest to a target protein. Using this technology we generated $Y_{730}NH_2Y$-α2 and $Y_{731}NH_2Y$-α2 and tested involvement of these residues in long-range radical propagation. The results demonstrate kinetically competent radical transfer from the $Y_{122}$. in β2 across the subunit interface and trapping of $NH_2Y_{730}$. or $NH_2Y_{731}$. This event is triggered by binding of substrate and effector. Steady state activity assays in conjunction with reactions with the suicide inhibitor $N_3ADP$ indicate that $Y_{730}NH_2Y$-α2 and $Y_{731}NH_2Y$-α2 are competent in nucleotide reduction. This implicates a hydrogen atom transfer mechanism for oxidation of $C_{439}$ by $NH_2Y_{730}$. Definitive evidence for activity of $NH_2Y$-α2s requires a detailed kinetic analysis of the decay of $NH_2Y$. and formation of N. with the mechanism-based inhibitor $N_3NDP$. These studies are currently in progress.

Supporting Information. Attempts at expression of $Y_{730}NH_2Y$-α2 from vectors pBAD-nrdA and pMJ1-nrdA under various conditions, expression gel of $Y_{730}NH_2Y$-α2 with pTrc-nrdA, purification gels of $NH_2Y$-α2s, SF UV-vis characterization and 10 s EPR spectrum of the reaction of $Y_{731}NH_2Y$-α2 with β2, CDP/ATP and EPR spectra for the reaction of $Y_{731}NH_2Y$-α2/β2 with $N_3ADP$ and dGTP. This material is available free of charge via the Internet at http://pubs.acs.org.

FIGURE LEGENDS

FIG. 1: The putative radical initiation pathway generated from the docking model of α2 and β2.[6] $Y_{356}$ is not visible in any structures because it lies on the disordered C-terminal tail of β2. Therefore, the distances from $Y_{356}$ to β2-$W_{48}$ and to α2-$Y_{731}$ are not known. Distances on the α2 side are from the structure determined by Uhlin and Eklund[6] and those on the β2 side are from the high-resolution structure of oxidized β2.[19]

FIG. 2: MALDI-TOF MS and SDS PAGE analysis of $K_7NH_2Y$—Z-domain. MALDI-TOF MS of purified $K_7NH_2Y$—Z-domain obtained under positive ionization mode. The m/z [M+H]$^+$ are indicated for the main peaks in the spectrum. They correspond to N-terminally cleaved Met form of $K_7NH_2Y$—Z-Domain (exp. 7814) and its acetylated form (exp. 7856), full-length $K_7NH_2Y$-His-Z-Domain (exp. 7945) and its acetylated form (exp. 7987). The inset shows the SDS gel of purified Z-domain after expression in the absence (lane 2) or presence (lane 3) of $NH_2Y$. The arrow designates the $K_7NH_2Y$—Z-domain band. Protein ladder and corresponding MW are shown in lane 1.

FIG. 3: Expression of $Y_{731}NH_2Y$-α2. Cells were grown in the presence or absence of IPTG and $NH_2Y$/DTT as indicated and the level of expression assessed by SDS PAGE. The position of protein bands for full-length cc and truncated cc are denoted by arrows.

FIG. 4: Reaction of $Y_{730}NH_2Y$-α2/ATP with wt β2/CDP monitored by EPR spectroscopy. The reaction components were mixed at 25° C. to yield final concentrations of 20 μM $Y_{730}NH_2Y$-α2β2, 1 mM CDP, and 3 mM ATP. After 10 s, the reaction was quenched in liquid $N_2$ and the EPR spectrum (solid line) was subsequently recorded at 77 K. Unreacted $Y_{122}$. (dotted line, 47% of total spin), was subtracted to reveal the spectrum of $NH_2Y_{730}$. (dashed line, 53% of total spin). The inset shows the reaction of $Y_{730}NH_2Y$-α2 with wt β2 in the absence of CDP/ATP.

FIG. 5: Microwave power dependence of $Y_{122}$. and $NH_2Y_{730}$. signal intensities. The EPR spectrum of the $Y_{122}$. and $NH_2Y_{730}$. was recorded as a function of microwave power, and the integrated intensity of each signal was plotted against the square root of power. Black lines represent fits to the data using eq 1[80] and yield $P_{1/2}$ of 28±4 mW (b=1.3±0.2) and 0.42±0.08 mW (b=1.2±0.2) for $Y_{122}$. (circles) and $NH_2Y_{730}$. (squares), respectively.

FIG. 6: Comparison of the $NH_2Y_{730}$. (dotted line, FIG. 4) and $NH_2Y_{731}$. (dashed line, FIG. 15).

FIG. 7: Point-by-point reconstruction of the UV-vis spectrum of $NH_2Y_{730}$. (circles) and $NH_2Y_{731}$. (squares). Prereduced $Y_{730}NH_2Y$-α2 and ATP in one syringe were mixed with wt β2 and CDP from another syringe, yielding final concentrations of 10 μM, 3 mM, 10 μM, and 1 mM, respectively. With $Y_{731}NH_2Y$-α2, the reaction was carried out at final concentrations of 9 μM $Y_{731}NH_2Y$-α2β2, 1 mM CDP, and 3 mM ATP. The absorption change was monitored in 5 nm intervals; at each λ, 2-4 time courses were averaged and corrected for the absorption of $Y_{122}$. using previously determined ∈ in this spectral range.[66,67] The corrected DOD was converted to ∈,[68] which was then plotted against λ.

FIG. 8: SF kinetics of $NH_2Y_{730}$. formation. Prereduced $Y_{730}NH_2Y$-α2 (20 μM) and CDP (2 mM) in one syringe were mixed in a 1:1 ratio with β2 (20 μM) and ATP (3 mM) from another syringe. A total of 7 traces were averaged at 325 and 410 nm monitoring $NH_2Y_{730}$. formation and $Y_{122}$. disappearance. Black lines indicate biexponential fits to the data (see Table 2 for kinetic parameters).

FIG. 9: Formation of N. from $N_3ADP$ upon incubation with $Y_{730}NH_2Y$-α2, β2, and dGTP. The reaction contained final concentrations of 20 μM $Y_{730}NH_2Y$-α2β2 (1.2 $Y_{122}$./β2), 1 mM $N_3ADP$, and 0.25 mM dGTP. After 20 s, it was freeze-quenched in liquid $N_2$, and its EPR spectrum was recorded. (A) Subtraction of N. (dotted line, 19% of total spin) from the observed spectrum (dashed line) yields the black trace, which contains the $Y_{122}$. and $NH_2Y_{730}$. signals. (B) Subtraction of $Y_{122}$. (dotted line, 43% of total) from the resulting spectrum in (A) reveals the spectrum of $NH_2Y_{730}$. (dashed line, 39% of total spin). See Table 4 for quantitation of the concentration of each radical species.

FIG. 10: Spectral comparison of N. (black), $Y_{122}$. (dotted line), and $NH_2Y_{730}$. (dashed line). The distinct features of N.

and $Y_{122}$., on the low field side of the spectrum, facilitate in deconvolution of the complex spectra in FIGS. 4, 9, 15, and 17.

FIG. 11: Mechanistic options for oxidation of $C_{439}$ by $NH_2Y_{730}$. (A) Stepwise electron transfer/proton transfer. The initial electron transfer event generates a distinct intermediate that contains a thiyl cation radical and an 3-aminotyrosinate ($NH_2Y_{730}^-$). Subsequent proton-transfer yields a neutral thiyl radical and $NH_2Y_{730}$. This reaction is highly disfavored (see text). (B) Orthogonal PCET. ET and proton transfer are coupled but the electron and proton have different destinations. The proton of $C_{439}$ is transferred orthogonally to a basic residue; its electron is transferred to $NH_2Y_{730}$., thus generating a $C_{439}$. and $NH_2Y_{730}$. (C) Co-linear PCET. Hydrogen-atom transfer from $C_{439}$ to $NH_2Y_{730}$. Proton and electron originate from and arrive at the same moiety.

Figure 12:
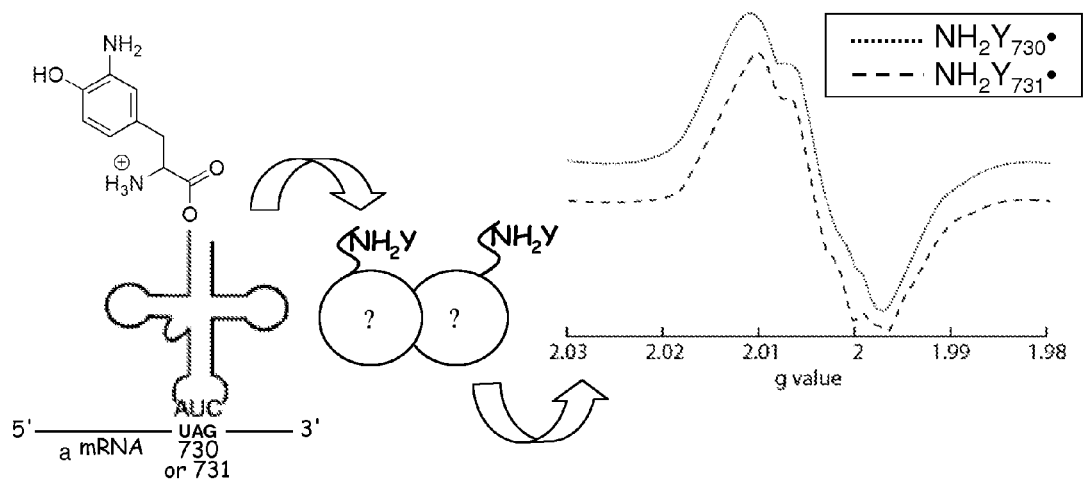
FIG. 12 provides a schematic graphic of the strategy used to determine the mechanistic roles of amino acids $Y_{730}$ and $Y_{731}$ in the α2 subunit of E. coli ribonucleotide reductase.

FIG. 12 provides a schematic graphic of the strategy used to determine the mechanistic roles of amino acids $Y_{730}$ and $Y_{730}$ in the α2 subunit of *E. coli* ribonucleotide reductase.

FIG. 13: Expression of $Y_{730}NH_2Y$-α2. Cells were grown in the presence or absence of IPTG and $NH_2Y$/DTT and at 25° or 37° C., as indicated, and the level of expression assessed by SDS PAGE. The position of protein bands for full-length α and truncated α are denoted by arrows.

FIG. 14: SDS PAGE analysis of purified $Y_{730}NH_2Y$-α2 (A) and $Y_{731}NH_2Y$-α2 (B). (A) Lanes (1) and (4), MW markers. The MW for each band is indicated. Lane (2), purified $Y_{730}NH_2Y$α2 (1.5 µg). Lane (3), purified wt α2 (1.5 µg). (B) Lane (1), MW markers. The MW for each band is indicated. Lane (2), purified $Y_{731}NH_2Y$-α2 (1.5 µg).

FIG. 15: Reaction of $Y_{731}NH_2Y$-α2/ATP with wt 132/CDP monitored by EPR. The reaction components were mixed at 25° C. to yield final concentrations of 20 µM $Y_{731}NH_2Y$-α2β2 complex, 1 mM CDP and 3 mM ATP. After 10 s, the reaction was quenched by hand-freezing in liquid $N_2$ and the EPR spectrum subsequently recorded at 77 K as described in the Methods section. Unreacted $Y_{122}$. (dotted line, 55% of total spin), was subtracted to reveal the spectrum of $NH_2Y_{730}$. (dashed line, 45% of total spin). Inset: Reaction of $Y_{730}NH_2Y$-α2 with wt 132 in the absence of CDP/ATP.

Figure 16:
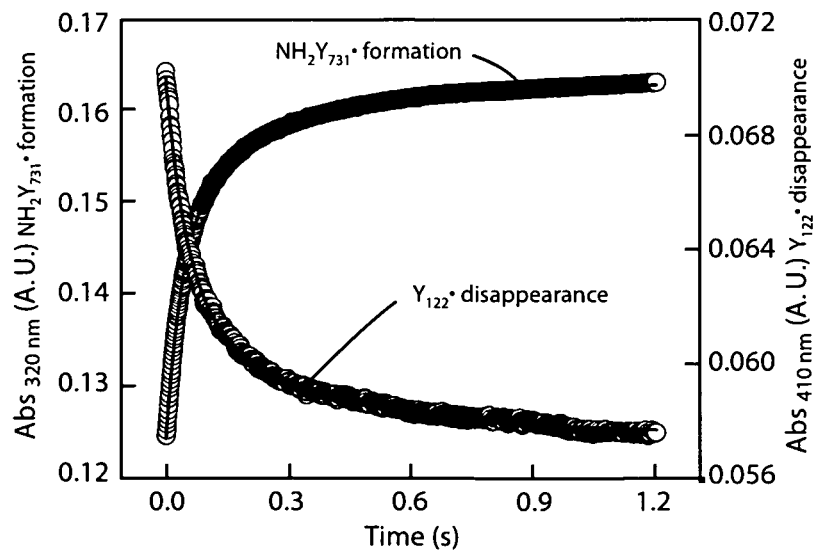
FIG. 16 depicts stopped flow kinetics of $NH_2Y_{731}$. formation.

FIG. 16: Kinetics of $NH_2Y_{731}$. formation. Pre-reduced $Y_{731}NH_2Y$-α2 (18 µM) and CDP (2 mM) in one syringe were mixed in a 1:1 ratio with 132 (18 µM) and ATP (3 mM) from another syringe. A total of 6 traces were averaged at 320 nm and 410 nm monitoring $NH_2Y_{731}$. formation and $Y_{122}$. disappearance. Black lines indicate bi-exponential fits to the data—see Table 2 for kinetic parameters.

Figure 17A:
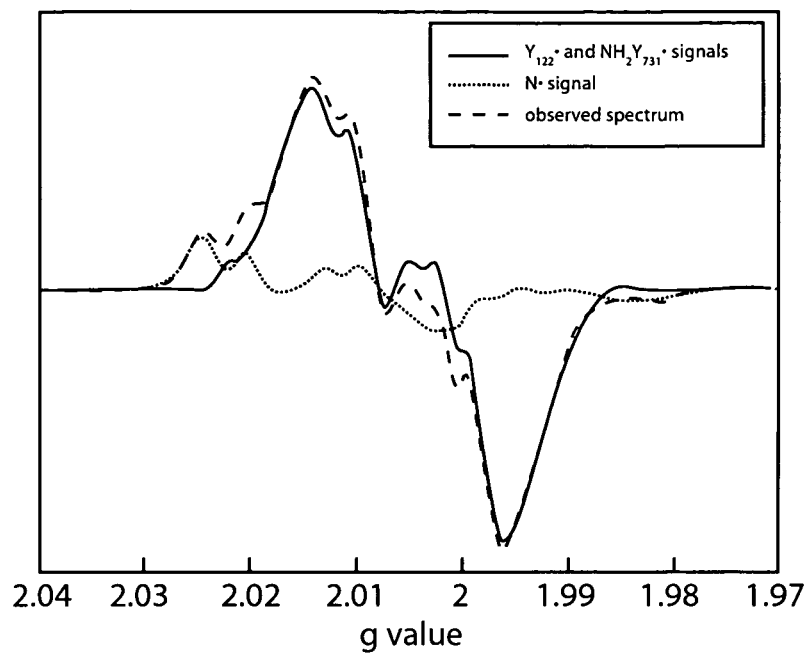
FIG. 17 shows the results of an $N_3$ADP assay for $Y_{731}NH_2Y$-α2.
Figure 17B:
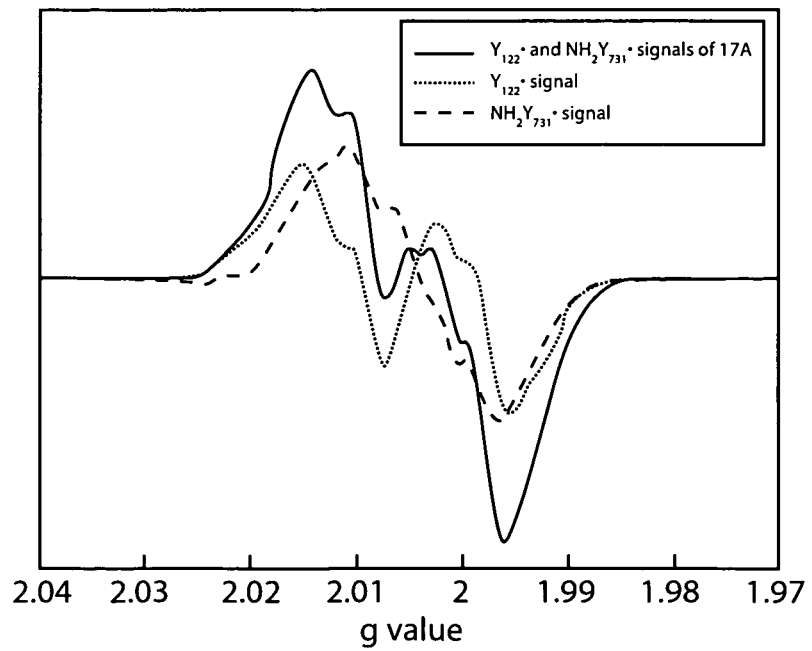

FIG. 17: $N_3$ADP Assay for $Y_{731}NH_2Y$-α2. The reaction contained final concentrations of 20 µM $Y_{731}NH_2Y$-α2β2 (1.2 $Y_{122}$./β2), 1 mM $N_3$ADP and 250 µM dGTP. After 20 s, it was freeze-quenched by hand in liquid $N_2$ and its EPR spectrum recorded. (A) Subtraction of N. (dotted line, 20% of total spin) from the observed spectrum (dashed line) yields the solid black trace, which contains $Y_{122}$. and $NH_2Y_{731}$. signals. (B) Subtraction of $Y_{122}$. (dotted line, 41% of total) from the resulting spectrum in (A) reveals the spectrum of $NH_2Y_{731}$. (dashed line, 39% of total spin). See Table 4 for quantitation of the concentration of each radical species.

REFERENCES

1. Stubbe, J.; van der Donk, W. A. *Chem. Rev.* 1998, 98, 705.
2. Jordan, A.; Reichard, P. *Annu. Rev. Biochem.* 1998, 67, 71.
3. Nordlund, P.; Reichard, P. *Annu. Rev. Biochem.* 2006, 75, 681.
4. Stubbe, J. *J. Biol. Chem.* 1990, 265, 5329.
5. Stubbe, J. *Proc. Natl. Acad. Soc. U.S.A.* 1998, 95, 2723.
6. Uhlin, U.; Eklund, H. *Nature* 1994, 370, 533.
7. Licht, S.; Gerfen, G. J.; Stubbe, J. *Science* 1996, 271, 477.
8. Logan, D. T., Andersson, J.; Sjöberg, B.-M.; Nordlund, P. *Science* 1999, 283, 1499.
9. Jiang, W.; Yun, D.; Saleh, L.; Barr, E. W.; Xing, G.; Hoffart, L. M.; Maslak, M. A.; Krebs, C.; Bollinger J. M. Jr. *Science* 2007, 316, 1188.
10. Brown, N. C.; Reichard, P. *J. Mol. Biol.* 1969, 46, 25.
11. Thelander, L. *J. Biol. Chem.* 1973, 248, 4591.
12. Wang, J.; Lohman, G. J.; Stubbe, J. *Proc. Natl. Acad. Soc. U.S.A.* 2007, in press.
13. Brown, N. C.; Reichard, P. *J. Mol. Biol.* 1969, 46, 39.
14. Ehrenberg, A.; Reichard, P. *J. Biol. Chem.* 1972, 247, 3485.
15. Sjöberg, B.-M.; Reichard, P.; Graslund, A.; Ehrenberg, A. *J. Biol. Chem.* 1978, 253, 6863.
16. Reichard, P.; Ehrenberg, A. *Science* 1983, 221, 514.
17. Eriksson, M.; Uhlin, U.; Ramaswamy, S.; Ekberg, M.; Regnstrom, K; Sjöberg, B.-M.; Eklund, H. *Structure* 1997, 5, 1077.
18. Nordlund, P.; Sjöberg, B.-M.; Eklund, H. *Nature* 1990, 345, 593.
19. Högbom, M.; Galander, M.; Andersson, M.; Kolberg, M.; Hofbauer, W.; Lassmann, G.; Nordlund, P.; Lendzian, F. *Proc. Natl. Acad. Sci.* 2003, 100, 3209.
20. Uppsten, M.; Farnegardh, M.; Domkin, V.; Uhlin U. *J. Mol. Biol.* 2006, 359, 365.
21. Stubbe, J.; Nocera, D. G.; Yee, C. S.; Chang, M. C. Y. *Chem. Rev.* 2003, 103, 2167.
22. Stubbe, J.; Riggs-Gelasco, P. *Trends Biochem. Sci.* 1998, 23, 438.
23. Lawrence, C. C.; Stubbe, J. *Curr. Opin. Chem. Biol.* 1998, 2, 650.
24. Marcus, R. A.; Sutin, N. *Biochim. Biophys. Acta* 1985, 811, 265.
25. Moser, C. C.; Keske, J. M.; Warncke, K.; Farid, R. S.; Dutton, P. L. *Nature* 1992, 355, 796.
26. Gray, H. B.; Winkler, J. R. *Annu. Rev. Biochem.* 1996, 65, 537.
27. Bennati, M.; Weber, A.; Antonic, J.; Perlstein, D. L.; Robblee, J.; Stubbe, J. *J. Am. Chem. Soc.* 2005, 125, 14988.
28. Thelander, L.; Larsson, B.; Hobbs, J.; Eckstein, F. *J. Biol. Chem.* 1976, 251, 1398.
29. Sjöberg, B.-M.; Graslund, A.; Eckstein, F. *J. Biol. Chem.* 1983, 258, 8060.
30. Salowe, S.; Bollinger, J. M. Jr.; Ator, M.; Stubbe, J.; McCraken. J.; Peisach, J.; Samano, M. C.; Robins, M. J. *Biochemistry* 1993, 32, 12749.
31. Fritscher, J.; Artin, E.; Wnuk, S.; Bar, G.; Robblee, J. H.; Kacprzak, S.; Kaupp, M.; Griffin, R. G.; Bennati, M.; Stubbe, J. *J. Am. Chem. Soc.* 2005, 127, 7729.
32. Bennati, M.; Robblee, J. H.; Mugnaini, V.; Stubbe, J.; Freed, J. H.; Borbat, P. *J. Am. Chem. Soc.* 2005, 127, 15014.
33. Climent, I.; Sjöberg, B.-M.; Huang, C. Y. *Biochemistry* 1992, 31, 4801.
34. Ekberg, M.; Sahlin, M.; Eriksson, M.; Sjöberg, B.-M.; *J. Biol. Chem.* 1996, 271, 20655.
35. Ekberg, M.; Birgander, P.; Sjöberg, B.-M.; *J. Bacteriol.* 2003, 185, 1167.
36. Yee, C. S.; Seyedsayamdost, M. R.; Chang, M. C.; Nocera, D. G.; Stubbe, J. *Biochemistry* 2003, 42, 14541.
37. Seyedsayamdost, M. R.; Yee, C. S.; Stubbe, J. *Nat. Protoc.* 2007, 2, 1225.
38. Seyedsayamdost, M. R.; Stubbe, J. *J. Am. Chem. Soc.* 2006, 128, 2522.
39. Seyedsayamdost, M. R.; Stubbe, J. *J. Am. Chem. Soc.* 2007, 129, 2226.

40. Seyedsayamdost, M. R.; Reece, S. Y.; Nocera, D. G.; Stubbe, J. *J. Am. Chem. Soc.* 2006, 128, 1569.
41. Yee, C. S.; Chang, M. C.; Ge, J.; Nocera, D. G.; Stubbe J. *J. Am. Chem. Soc.* 2003, 125, 10506.
42. Reece, S. Y.; Seyedsayamdost, M. R.; Stubbe, J.; Nocera, D. G. *J. Am. Chem. Soc.* 2006, 128, 13654.
43. Seyedsayamdost, M. R.; Yee, C. S.; Reece, S. Y.; Nocera, D. G.; Stubbe, J. *J. Am. Chem. Soc.* 2006, 128, 1562.
44. Chang, M. C.; Yee, C. S.; Stubbe, J.; Nocera, D. G. *Proc. Natl. Acad. Sci. U.S.A.* 2004, 101, 6882.
45. Reece, S. Y.; Seyedsayamdost, M. R.; Stubbe, J.; Nocera, D. G *J. Am. Chem. Soc.* 2007, 129, 8500.
46. Wang, L.; Brock, A.; Herberich, B.; Schultz, P. G. *Science* 2001, 292, 498.
47. Wang, L.; Schultz, P. G. *Angew. Chem. Int. Ed. Engl.* 2004, 44, 34.
48. Xie, J.; Schultz, P. G. *Methods* 2005, 36, 227.
49. Wang, L.; Xie, J.; Schultz, P. G. *Annu. Rev. Biophys. Biomol. Struct.* 2006, 35, 225.
50. Xie, J.; Schultz, P. G. *Nat. Rev. Mol. Cell. Biol.* 2006, 7, 775.
51. DeFelippis, M. R.; Murthy, C. P.; Broitman, F.; Weinraub, D.; Faraggi, M.; Klapper, M. H. *J. Phys. Chem.* 1991, 95, 3416.
52. Jovanovic, S. J.; Steenken, S.; Tosic, M.; Marjanovic, B.; Simic, M. G. *J. Am. Chem. Soc.* 1994, 116, 4846.
53. Chivers, P. T.; Prehoda, K. E.; Volkman, B. F.; Kim, B.-M.; Markley, J. L.; Raines, R. T. *Biochemistry* 1997, 36, 14985.
54. Russel, M.; Model, P. *J. Bacteriol.* 1985, 163, 238.
55. Salowe, S. P.; Stubbe, J. *J. Bacteriol.* 1986, 165, 363.
56. Santoro, S. W.; Wang, L.; Herberich, B.; King, D. S.; Schultz, P. G. *Nat. Biotechnol.* 2002, 20, 1044.
57. Wang, L.; Zhang, Z.; Brock, A.; Schultz, P. G. *Proc. Natl. Acad. Sci. U.S.A.* 2003, 100, 56.
58. Chin, J. W.; Martin, A. B.; King, D. S.; Wang, L.; Schultz, P. G. *Proc. Natl. Acad. Sci. U.S.A.* 2002, 99, 11020.
59. Zhang, Z.; Wang, L.; Brock, A.; Schultz, P. G. *Angew. Chem. Int. Ed. Engl.* 2002, 41, 2840.
60. Mao, S. S.; Johnston, M. I.; Bollinger, J. M.; Stubbe J. *Proc. Natl. Acad. Sci. U.S.A.* 1989, 86, 1485.
61. Zhang, Z.; Smith, B. A. C.; Wang, L.; Brock, A.; Cho, C.; Schultz, P. G.; *Biochemistry* 2003, 42, 6735.
62. Salowe, S. P. *Ph.D. Thesis*. Massachusetts Institute of Technology, Cambridge, Mass., 1992.
63. Ryu, Y.; Schultz, P. G. *Nat. Methods* 2006, 3, 263.
64. Farrell, I. S.; Toroney, R.; Hazen, J. L.; Mehl, R. A.; Chin, J. W. *Nat. Methods* 2005, 2, 377.
65. Palmer, G. *Methods Enzymol.* 1967, 10, 595.
66. Gräslund, A.; Sahlin, M.; Sjöberg, B.-M. *Environ. Health Perspect.* 1985, 64, 139.
67. Nyholm, S.; Thalander, L.; Graslund, A. *Biochemistry* 1993, 32, 11569.
68. Bollinger Jr., J. M.; Tong, W. H.; Ravi, N.; Huynh, B. H.; Edmondson, D. E.; Stubbe, J. *Methods Enzymol.* 1995, 258, 278-303.
69. Wang, L.; Schultz, P. G. *Chem. Biol.* 2001, 8, 883.
70. Liu, D. R.; Schultz, P. G. *Proc. Natl. Acad. Soc. U.S.A.* 1999, 96, 4780.
71. Zhang, Y.; Wang, L.; Schultz, P. G.; Wilson, I. A. *Protein Sci.* 2005, 14, 1340.
72. Turner, J. M.; Graziano, J.; Spraggon, G.; Schultz, P. G. *Proc. Natl. Acad. Soc. U.S.A.* 2006, 103, 6483.
73. Nilsson, B.; Moks, T.; Jansson, B.; Abrahmsen, L.; Elmblad, A.; Holmgren, E.; Henrichson, C.; Jones, T. A.; Uhlen, M. *Protein Eng.* 1987, 1, 107.
74. Fontecave, M.; Mulliez, E.; Logan D. T. *Prog. Nucleic Acid Res. Mol. Biol.* 2002, 72, 95.
75. Rosenkranz, H. S.; Garro, A. J.; Levy, J. A.; Carr, H. S. *Biochim. Biophys. Acta* 1966, 114,501.
76. Karlsson, M.; Sahlin, M.; Sjöberg, B.-M. *J. Biol. Chem.* 1992, 267, 12622.
77. Jackson, J. C.; Duffy, S. P.; Hess, K. R.; Mehl, R. A. *J. Am. Chem. Soc.* 2006, 128, 11124.
78. Amann, E.; Ochs, B.; Abel, K. J. *Gene* 1987, 61, 41.
79. A more detailed analysis of the new radical species will be presented elsewhere.
80. Chen-Barrett, Y.; Harrison, P. M.; Treffry, A.; Quail, M. A.; Arosio, P.; Santambrogio, P.; Chasteen, N. D. *Biochemistry* 1995, 24, 7847.
81. Sahlin, M.; Petersson, L.; Graslund, A.; Ehrenberg, A.; Sjöberg, B.-M.; Thelander, L. *Biochemistry* 1987, 26, 5541.
82. Gerfen, G. J.; van der Donk, W. A.; Yu, G.; McCarthy, J. R.; Jarvi, E. T.; Matthews, D. P.; Farrar, C.; Griffin, R. G.; Stubbe, J. *J. Am. Chem. Soc.* 1998, 120, 3823.
83. Ge, J.; Yu, G.; Ator, M. A.; Stubbe, J. *Biochemistry* 2003, 42, 10071.
84. Rapid chemical quench studies monitoring dCDP formation with intein-generated wt β2, no longer show a burst of dCDP formation (as with wt (32) but exhibit a single rate constant of ~1 $s^{-1}$ (M. Seyedsayamdost, J. Stubbe, unpublished results). Thus, the slow phase observed with DOPA-β2 could also be kinetically competent in turnover.
85. Craw, M.; Chedekel, M. R.; Truscott, T. G.; Land, E. J. *Photochem. Photobiol.* 1984, 39, 155-159.
86. van der Donk, W. A.; Stubbe, J.; Gerfen, G. J.; Bellew, B. F.; Griffin, R. G. *J. Am. Chem. Soc.* 1995, 117, 8908.
87. Hooker, J. M.; Kovacs, E. W.; Francis, M. B. *J. Am. Chem. Soc.* 2004, 126, 3718.
88. Kovacs, E. W.; Hooker, J. M.; Romanini, D. W.; Holder, P. G.; Berry, K. E.; Francis, M. B. *Bioconjug. Chem.* 2007, 18, 1140.
89. Felix, C. C.; Sealy, R. C. *J. Am. Chem. Soc.* 1981, 103, 2831.
90. Neta, P.; Fessenden, R. W. *J. Phys. Chem.* 1974, 78, 523.
91. Previous computational studies on o-aminophenol have shown that the BDE of the phenolic hydroxyl group is lower than that of the amine. EPR studies on o-aminophenol are in line with these calculations demonstrating the presence of two N-bound protons in the oxidized state (see refs. 88 and 94). Our own preliminary EPR simulations and DFT calculations also suggest that the structure of the radical is that shown in Scheme 1 (M. Seyedsayamdost, M. Bennati, J. Stubbe, unpublished results).
92. Cukier, R. I.; Nocera, D. G. *Annu. Rev. Phys. Chem.* 1998, 49, 337.
93. Mayer, J. M.; Rhile, I. J. *Biochim. Biophys. Acta* 2004, 1655, 51.
94. Reece, S. Y.; Hodgkiss, J. M.; Stubbe, J.; Nocera D. G. *Philos. Trans. R. Soc. Lond. B Biol. Sci.* 2006, 361, 1351.
95. Borges dos Santos, R. M.; Martinho Simões, J. A. *J. Phys. Chem. Ref Data* 1998, 27, 707.
96. Wright, J. S.; Johnson, E. R.; DiLabio, G. A. *J. Am. Chem. Soc.* 2001, 123, 1173.
97. Bakalbassis, E. G.; Lithoxoidou, A. T.; Vafiadis, A. P. *J. Phys. Chem. A* 2006, 110, 11151.

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A cell comprising:

a recombinant nucleic acid that is derived from a reductase nucleic acid that encodes one or more polypeptide chain of a reductase enzyme, the recombinant nucleic acid comprising a selector codon;

the cell further comprising an orthogonal aminoacyl tRNA synthetase (O-RS) and an orthogonal tRNA (O-tRNA) that recognizes the selector codon, wherein the O-RS preferentially aminoacylates the O-tRNA with 3-aminotyrosine and wherein the reductase is or is derived from an E. coli ribonucleotide reductase comprising an $NH_2Y$ mutation at one or more of:

(a) Y730 of an α2 subunit of the E. coli ribonucleotide reductase;

(b) Y731 of an α2 subunit of the E. coli ribonucleotide reductase; or (c) Y122 of a β2 subunit of the E. coli ribonucleotide reductase.

2. The cell of claim 1, wherein the nucleic acid encodes one or more polypeptide chain homologous to a polypeptide chain of a class I or class IV ribonucleotide reductase.

3. The cell of claim 1, comprising 3-aminotyrosine.

4. A method of determining a function of a selected amino acid residue in a reductase, the method comprising:

mutating the selected amino acid residue to 3-aminotyrosine ($NH_2Y$) to produce a recombinant mutant reductase that comprises $NH_2Y$ at a site corresponding to the selected amino acid and wherein the reductase is or is derived from an E. coli ribonucleotide reductase comprising an $NH_2Y$ mutation at one or more of:

(a) Y730 of an α2 subunit of the E. coli ribonucleotide reductase;

(b) Y731 of an α2 subunit of the E. coli ribonucleotide reductase; or (c) Y122 of a β2 subunit of the E. coli ribonucleotide reductase;

mixing the recombinant reductase with one or more substrates or effectors of the reductase; and, detecting formation of $NH_2Y$.

5. The method of claim 4, wherein the substrate comprises CDP ADP, GDP, or UDP and the effector comprises ATP.

6. The method of claim 4, comprising reducing the reductase prior to said mixing.

7. The method of claim 6, wherein reducing the recombinant reductase comprises purifying the recombinant reductase from a cell or cell culture that expresses the recombinant reductase, and incubating the resulting purified reductase with a reducing agent.

8. The method of claim 4, wherein detecting formation of $NH_2Y$ comprises determining an EPR spectra for the $NH_2Y$ residue in the reductase.

9. The method of claim 4, wherein detecting formation of $NH_2Y$ comprises performing stopped flow spectroscopy after said mixing to determine kinetics of $NH_2Y$ formation.

10. The method of claim 4, wherein detecting formation of $NH_2Y$ comprises performing rapid freeze quench EPR after said mixing to determine kinetics of $NH_2Y$ formation.

* * * * *

UNITED STATES PATENT AND TRADEMARK OFFICE
CERTIFICATE OF CORRECTION

PATENT NO. : 8,673,591 B2  
APPLICATION NO. : 12/734226  
DATED : March 18, 2014  
INVENTOR(S) : Seyedsayamdost et al.

Page 1 of 1

It is certified that error appears in the above-identified patent and that said Letters Patent is hereby corrected as shown below:

In the Specification

Column 1, Lines 15-20, the paragraph SPONSORED RESEARCH AND DEVELOPMENT should be changed to:
-- STATEMENT OF GOVERNMENT LICENSE RIGHTS
This invention was made with government support under grant numbers GM062159 and GM029595 awarded by the National Institutes of Health. The government has certain rights in the invention. --

Signed and Sealed this
Seventh Day of April, 2020

Andrei Iancu
*Director of the United States Patent and Trademark Office*

SEQUENCE LISTING

```
<160> NUMBER OF SEQ ID NOS: 6

<210> SEQ ID NO 1
<211> LENGTH: 39
<212> TYPE: DNA
<213> ORGANISM: Artificial Sequence
<220> FEATURE:
<223> OTHER INFORMATION: Oligonucleotide primer for PCR

<400> SEQUENCE: 1
ataattggta cccaaaaaca ggtacgacat acatgaatc                      39

<210> SEQ ID NO 2
<211> LENGTH: 37
<212> TYPE: DNA
<213> ORGANISM: Artificial Sequence
<220> FEATURE:
<223> OTHER INFORMATION: Oligonucleotide primer for PCR

<400> SEQUENCE: 2
gctgcaggtc gactctagag gatccccct tcttatc                         37

<210> SEQ ID NO 3
<211> LENGTH: 30
<212> TYPE: DNA
<213> ORGANISM: Artificial Sequence
<220> FEATURE:
<223> OTHER INFORMATION: Oligonucleotide primer for PCR

<400> SEQUENCE: 3
ggtcaaaaca ctgtagtatc agaacacccg                                30

<210> SEQ ID NO 4
<211> LENGTH: 30
<212> TYPE: DNA
<213> ORGANISM: Artificial Sequence
<220> FEATURE:
<223> OTHER INFORMATION: Oligonucleotide primer for PCR

<400> SEQUENCE: 4
cgggtgttct gatactacag tgttttgacc                                30

<210> SEQ ID NO 5
<211> LENGTH: 30
<212> TYPE: DNA
<213> ORGANISM: Artificial Sequence
<220> FEATURE:
<223> OTHER INFORMATION: Oligonucleotide primer for PCR

<400> SEQUENCE: 5
ggtcaaaaca ctgtattagc agaacacccg                                30

<210> SEQ ID NO 6
<211> LENGTH: 30
<212> TYPE: DNA
<213> ORGANISM: Artificial Sequence
<220> FEATURE:
<223> OTHER INFORMATION: Oligonucleotide primer for PCR
```

```
<400> SEQUENCE: 6
cgggtgttct gctaatacag tgttttgacc                                            30
```